(12) United States Patent
Kwon et al.

(10) Patent No.: US 10,682,415 B2
(45) Date of Patent: Jun. 16, 2020

(54) THERMOGEL FORMULATION FOR COMBINATION DRUG DELIVERY

(71) Applicant: Wisconsin Alumni Research Foundation, Madison, WI (US)

(72) Inventors: Glen S. Kwon, Madison, WI (US); Hyunah Cho, Madison, WI (US)

(73) Assignee: WISCONSIN ALUMNI RESEARCH FOUNDATION, Madison, MI (US)

( * ) Notice: Subject to any disclaimer, the term of this patent is extended or adjusted under 35 U.S.C. 154(b) by 630 days.

(21) Appl. No.: 14/337,929

(22) Filed: Jul. 22, 2014

(65) Prior Publication Data
US 2015/0025106 A1    Jan. 22, 2015

Related U.S. Application Data

(60) Provisional application No. 61/900,648, filed on Nov. 6, 2013, provisional application No. 61/857,055, filed on Jul. 22, 2013.

(51) Int. Cl.
*A61K 31/337* (2006.01)
*A61K 31/436* (2006.01)
(Continued)

(52) U.S. Cl.
CPC ............ *A61K 47/34* (2013.01); *A61K 9/0019* (2013.01); *A61K 9/06* (2013.01); *A61K 31/337* (2013.01);
(Continued)

(58) Field of Classification Search
CPC ...... A61K 9/06; A61K 47/34; A61K 2300/00; A61K 9/0019; A61K 31/337; A61K 31/436; A61K 31/395; A61P 35/00
See application file for complete search history.

(56) References Cited

U.S. PATENT DOCUMENTS 4,938,949 A    7/1990   Borch et al.
5,399,726 A    3/1995   Holton et al.
(Continued)

FOREIGN PATENT DOCUMENTS

WO    WO-02/066019    8/2002
WO    WO-2004/026280  4/2004
(Continued)

OTHER PUBLICATIONS

Banerji, U. et al., "A pharmacokinetically (PK)—pharmacodynamically (PD) guided phase I trial of the heat shock protein 90 (HSP90) inhibitor 17-allylamino,17-demethoxygeldanamycin (17AAG)," Proc. Am. Soc. Clin. Oncol., 2003, vol. 22, Abstract 797, 2 pages.
(Continued)

*Primary Examiner* — Theodore R. West
(74) *Attorney, Agent, or Firm* — Foley & Lardner LLP

(57) ABSTRACT

The invention provides a drug delivery system for a combination of therapeutic agents. The system includes a water soluble biodegradable ABA-type triblock copolymer that possesses thermosensitive gelation properties. The system can form a stable thermogel that includes a combination of therapeutic agents including, for example, rapamycin, paclitaxel, and 17-AAG. After administration to a subject, the drugs are released at a controlled rate from the thermogel, which biodegrades into non-toxic components. The polymer system can also function to increase the solubility and stability of drugs in the composition.

25 Claims, 12 Drawing Sheets

(51) Int. Cl.
A61K 31/395 (2006.01)
A61K 9/06 (2006.01)
A61K 47/34 (2017.01)
A61K 9/00 (2006.01)
A61P 35/00 (2006.01)

(52) U.S. Cl.
CPC .......... A61K 31/395 (2013.01); A61K 31/436 (2013.01); A61P 35/00 (2018.01)

(56) References Cited

U.S. PATENT DOCUMENTS

| | | | |
|---|---|---|---|
| 5,470,866 | A | 11/1995 | Kingston et al. |
| 5,654,447 | A | 8/1997 | Holton et al. |
| 6,004,573 | A | 12/1999 | Rathi et al. |
| 6,004,973 | A | 12/1999 | Guitard et al. |
| 6,107,332 | A | 8/2000 | Ali et al. |
| 6,118,011 | A | 9/2000 | Mayhew et al. |
| 6,136,961 | A | 10/2000 | Dordick et al. |
| 6,197,781 | B1 | 3/2001 | Guitard et al. |
| 6,201,072 | B1 * | 3/2001 | Rathi .............. A61K 9/0024 424/425 |
| 6,384,046 | B1 | 5/2002 | Schuler et al. |
| 7,091,213 | B2 | 8/2006 | Metcalf et al. |
| 7,135,190 | B2 | 11/2006 | Piao et al. |
| 2001/0010920 | A1 | 8/2001 | Molnar-Kimber et al. |
| 2005/0101656 | A1 | 5/2005 | Tian et al. |
| 2005/0256097 | A1 | 11/2005 | Zhong et al. |
| 2006/0019941 | A1 | 1/2006 | Adams et al. |
| 2006/0251710 | A1 | 11/2006 | Kwon et al. |
| 2007/0270396 | A1 | 11/2007 | Santi et al. |
| 2008/0207644 | A1 | 8/2008 | Sonis et al. |
| 2011/0076308 | A1 * | 3/2011 | Kwon ............... A61K 9/0019 424/400 |

FOREIGN PATENT DOCUMENTS

| | | |
|---|---|---|
| WO | WO-2005/011688 | 2/2005 |
| WO | WO-2005/070393 | 8/2005 |
| WO | WO-2006/086172 | 8/2006 |
| WO | WO-2006/089312 | 8/2006 |
| WO | WO-2006/095185 | 9/2006 |
| WO | WO-2011/025838 | 3/2011 |

OTHER PUBLICATIONS

Cho, Hyunah et al., "Poly(ethylene glycol)-block-poly(ε-caprolactone) micelles for combination drug delivery: Evaluation of paclitaxel, cyclopamine and gossypol in intraperitoneal xenograft models of ovarian cancer," J Controlled Release, (Feb. 28, 2013), vol. 166, Issue 1, pp. 1-9.
DiZerega, Gere S. et al., "Peritoneal repair and post-surgical adhesion formation," Hum Reprod Update, (2001), vol. 7, No. 6, pp. 547-555.
Elstad, Nancy L. et al., "OncoGel (ReGel/paclitaxel)—Clinical applications for a novel paclitaxel delivery system," Adv. Drug Del. Rev., (Aug. 10, 2009), vol. 61, Issue 10, pp. 785-794.
Fung, A.S., et al., "Concurrent and Sequential Administration of Chemotherapy and the Mammalian Target of Rapamycin Inhibitor Temsirolimus in Human Cancer Cells and Xenografts," Sep. 1, 2009, Clin. Cancer Res., vol. 15, No. 17, pp. 5389-5395.
Gao, Yuan et al., "A thermo-sensitive PLGA-PEG-PLGA hydrogel for sustained release of docetaxel," J Drug Target, (Aug. 2011), vol. 19, No. 7, pp. 516-527.
Gao, Yuan et al., "PLGA-PEG-PLGA hydrogel for ocular drug delivery of dexamethasone acetate," Drug Dev Ind Pharm, (Oct. 2010), vol. 36, No. 10, pp. 1131-1138.
Ge, J. et al., "Design, synthesis, and biological evaluation of hydroquinone derivatives of 17-amino-17-demethoxygeldanamycin as potent, water-soluble inhibitors of Hsp90," J. Med. Chem, (Jul. 27, 2006), vol. 49, No. 15, pp. 4606-4615.
Goetz, M., et al., "A phase I trial of 17-Allyl-Amino-Geldanamycin (17-AAG) in patients with advanced cancer," Eur. J. Cancer, Nov. 20, 2002, vol. 38, Supp. 7, pp. S54-S55.
Hamilton, Chad A. et al., "Intraperitoneal chemotherapy for ovarian cancer," Current Opinion in Oncology, (Sep. 2006), vol. 18, Issue 5, pp. 507-515.
Hidalgo et al., "The rapamycin-sensitive signal transduction pathway as a target for cancer therapy." Oncogene, 2000, 19, pp. 6680-6686.
Jeong, Byeongmoon et al., "Biodegradable block copolymers as injectable drug-delivery systems," Nature, (Aug. 28, 1997), vol. 388, pp. 860-862.
Jeong, Byeongmoon et al., "Drug release from biodegradable injectable thermosensitive hydrogel of PEG013PLGA013PEG triblock copolymers," J. Controlled Release, (Jan. 3, 2000), vol. 63, Issues 1-2, pp. 155-163.
Jeong, Byeongmoon et al., "Thermosensitive sol-gel reversible hydrogels," Adv. Drug Delivery Rev., (Jan. 17, 2002), vol. 54, Issue 1, pp. 37-51.
Lu, Ze et al., "Intraperitoneal therapy for peritoneal cancer," Future Oncol., (Oct. 2010), vol. 6, No. 10, pp. 1625-1641.
Lukas, George et al., "The Route of Absorption of Intraperitoneally Administered Compounds," J Pharmacol Exp Ther, (Sep. 1971), vol. 178, No. 3, pp. 562-566.
Markman, Maurie, "Intraperitoneal antineoplastic drug delivery: rationale and results," The Lancet Oncology, vol. 4, Issue 5, (May 2003), pp. 277-283.
Neshat, Mehran S. et al., "Enhanced sensitivity of PTEN-deficient tumors to inhibition of FRAP/mTOR," PNAS, (Aug. 28, 2001), vol. 98, No. 19, pp. 10314-10319.
Qiao, Mingxi et al., "Injectable biodegradable temperature-responsive PLGA-PEG-PLGA copolymers: Synthesis and effect of copolymer composition on the drug release from the copolymer-based hydrogels," Int J Pharmaceutics, (Apr. 27, 2005), vol. 294, Issues 1-2, pp. 103-112.
Shin, Ho-Chul et al., "A 3-in-1 Polymeric Micelle Nanocontainer for Poorly Water-Soluble Drugs," Mol Pharmaceut, (2011), vol. 8, No. 4, pp. 1257-1265.
Van Goor, H., "Consequences and complications of peritoneal adhesions," Colorectal Dis, (Oct. 2007), vol. 9, Suppl. 2, pp. 25-34.
Yeo, Yoon et al., "Polymers in the prevention of peritoneal adhesions," Eur J Pharm Biopharm, (Jan. 2008), vol. 68, No. 1, pp. 57-66.
Yu, L et al., "Injectable hydrogels as unique biomedical materials," Chem Soc Rev, (Aug. 2008), vol. 37, No. 8, pp. 1473-1481.
Yu, Lin et al., "The thermogelling PLGA-PEG-PLGA block copolymer as a sustained release matrix of doxorubicin," Biomater Sci-Uk, (2013), vol. 1, pp. 411-420.

* cited by examiner

THERMOGEL FORMULATION FOR COMBINATION DRUG DELIVERY

CROSS-REFERENCE TO RELATED APPLICATIONS

This application claims priority to U.S. Provisional Patent Application Nos. 61/857,055, filed on Jul. 22, 2013, and 61/900,648, filed on Nov. 6, 2013, the entire contents of which are incorporated herein by reference.

GOVERNMENT SUPPORT

This invention was made with government support under CA161537 awarded by the National Institutes of Health. The government has certain rights in the invention.

BACKGROUND OF THE INVENTION

As cancer research progresses, it is increasingly evident that single drug formulations provide only limited treatment success. Patients would therefore benefit from the development of suitable combination therapies. One of the most important requirements of combination therapy is a simple and efficacious drug delivery system, particularly for poorly water soluble drugs.

Many currently used chemotherapeutics are poorly water soluble, which significantly complicates the process of partnering the chemotherapeutic with a suitable delivery system. Combining two or three drugs in a formulation presents additional challenges in clinical practice because of compatibility and stability issues. Safer and more effective delivery of drug combinations relies on the development of biocompatible delivery systems capable of solubilizing the drug combination without using harsh surfactants or excipients. Furthermore, biocompatible delivery systems capable of releasing drug combinations at predictable and comparable rates would significantly aid their clinical applications. Finally, stable and biocompatible drug formulations that improve bioavailability without causing toxicity are urgently needed in the field of cancer research and therapy.

Accordingly, stable and biocompatible drug delivery systems that improve bioavailability without causing toxicity are needed for improving cancer therapy. Effective drug delivery systems for solubilizing combinations of anticancer agents are also needed. An effective combination drug therapy regimen that targets more than one cancer cell growth mechanistic pathway would also significantly aid cancer research and the development of effective clinical therapies.

SUMMARY

The invention provides stable solutions and thermosensitive hydrogels (i.e., thermogels) containing certain drug combinations. The thermogels can be formed from water soluble, low molecular weight, thermosensitive, biodegradable block copolymers having a high weight percentage of hydrophobic blocks. The polymers used to form the thermogel are thermosensitive biodegradable triblock copolymers based on poly(lactide-co-glycolide) and polyethylene glycol blocks, as described herein. These thermogel drug delivery systems are based block copolymers of relatively low molecular weight and relatively high hydrophobic block polymer content, which exist as solutions at approximately 5° C. (and several degrees below) to about 10° C., about 15° C., about 20° C., or about 25° C., in water. However, when the temperature of the solution is raised to about body temperature (typically 37° C. for humans), the polymers of the composition spontaneously interact to form semisolid hydrogels (i.e., gels) that contain high percentages of water entrapped within the gel network, yet are substantially insoluble in water.

Accordingly, the invention provides a composition comprising a PLGA-PEG-PLGA triblock copolymer, water, and a combination of therapeutic agents. The composition can be a non-flowing thermosensitive hydrogel at and above 22° C. and a free-flowing solution below about 10° C.; where the sum of the molecular weights of the PLGA blocks of the triblock copolymer is more than twice the molecular weight of the PEG block; the combination of therapeutic agents is at least two of paclitaxel, 17-AAG, and rapamycin; and/or the drug release $t_{1/2}$ of the non-flowing thermosensitive hydrogel at 37° C. is about 10 hours, and each of the drugs of the non-flowing thermosensitive hydrogel at 37° C. has equivalent drug release kinetics.

The concentration of each therapeutic agent in the composition can be about 9 mg/mL to about 20 mg/mL. In one embodiment, the concentration of paclitaxel in the composition is about 4 mg/mL to about 8 mg/mL. In some embodiments, the concentration of 17-AAG in the composition is about 4 mg/mL to about 8 mg/mL. In various embodiments, the concentration of rapamycin in the composition is about 2 mg/mL to about 6 mg/mL.

In one specific embodiment, the combination of therapeutic agents is paclitaxel, 17-AAG, and rapamycin.

In another specific embodiment, the combination of therapeutic agents is paclitaxel and 17-AAG.

In another specific embodiment, the combination of therapeutic agents is paclitaxel, and rapamycin.

In another specific embodiment, the combination of therapeutic agents is 17-AAG, and rapamycin.

The PLGA-PEG-PLGA triblock copolymer can have an average molecular weight of about 3 kDa to about 5 kDa. For example, the PLGA-PEG-PLGA triblock copolymer may be $PLGA_{1.5K}$-$PEG_{1K}$-$PLGA_{1.5K}$ triblock copolymer, wherein each $PLGA_{1.5K}$ is $PLGA_{1.5KDa}$ and $PEG_{1K}$ is $PEG_{1KDa}$.

In another embodiment, the polydispersity index of the thermosensitive hydrogel may be about 0.3 to about 0.5.

The invention also provides a method for killing or inhibiting the growth of cancer cells comprising contacting cancer cells with an effective lethal or inhibitory amount of a thermogel composition described herein, wherein the composition is in the form of a non-flowing gel and each of the drugs of the non-flowing has equivalent drug release kinetics, thereby killing the cancer cells or inhibiting their growth.

The contacting can be carried out at or above 22° C. and the composition can be in the form of a non-flowing gel. The cancer cells can be, for example, brain cancer cells, breast cancer cells, esophageal cancer cells, head and neck cancer cells, ovarian cancer cells, or pancreatic cancer cells. The two or three drugs in the composition can provide synergistic cytotoxicity toward the cancer cells.

The invention further provides a method of treating a solid tumor comprising locally administering an effective anticancer amount of a composition described herein to a subject in need thereof, wherein the amount of therapeutic agents administered to the subject would cause systemic toxicity of administered orally or intravenously, and wherein the local administration does not cause systemic toxicity.

In one specific embodiment, the combination of therapeutic agents is paclitaxel, 17-AAG, and rapamycin.

In another specific embodiment, the combination of therapeutic agents is paclitaxel and 17-AAG.

In another specific embodiment, the combination of therapeutic agents is paclitaxel and rapamycin.

In another specific embodiment, the combination of therapeutic agents is 17-AAG and rapamycin.

The invention yet further provides a method of preparing a composition as described herein comprising combining an aqueous solution of PLGA-PEG-PLGA triblock copolymer and an alcoholic solution of at least two of paclitaxel, 17-AAG, and rapamycin at a temperature above about 50° C., to for a mixture, lyophilizing the mixture to provide a powder or cake, and rehydrating the powder or cake with water at a temperature of less than about 10° C., to provide a free-flowing solution capable of forming a stable thermogel. In some embodiments, the PLGA-PEG-PLGA triblock copolymer is a $PLGA_{1.5K}$-$PEG_{1K}$-$PLGA_{1.5K}$ triblock copolymer and the alcohol of the alcoholic solution is t-butanol.

The invention provides compositions as described herein for use in medical therapy. The medical therapy can be treating cancer, for example, breast cancer (e.g., lymph node metastasis), lung cancer, prostate cancer, colon cancer, and particularly brain cancer, esophageal cancer, head and neck cancer, ovarian cancer, and pancreatic cancer, as well as other cancer conditions recited herein. The thermogel compositions described herein can be locally administered to a subject by a variety of means, including by parenteral, ocular, topical, vaginal, transurethral, rectal, nasal, oral, or aural administration. The invention also provides for the use of a composition as described herein for the manufacture of a medicament to treat a disease in a mammal, for example, cancer in a human. The medicament can further include a pharmaceutically acceptable diluent, excipient, or carrier.

BRIEF DESCRIPTION OF THE DRAWINGS

The following drawings form part of the specification and are included to further demonstrate certain embodiments or various aspects of the invention. In some instances, embodiments of the invention can be best understood by referring to the accompanying drawings in combination with the detailed description presented herein. The description and accompanying drawings may highlight a certain specific example, or a certain aspect of the invention. However, one skilled in the art will understand that portions of the example or aspect may be used in combination with other examples or aspects of the invention.

FIG. 4A demonstrates the release kinetics for PTX/RAPA; FIG. 4B demonstrates the release kinetics for PTX/17-AAG; and FIG. 4C demonstrates the release kinetics for RAPA/17-AAG.

DETAILED DESCRIPTION

Figure 1:
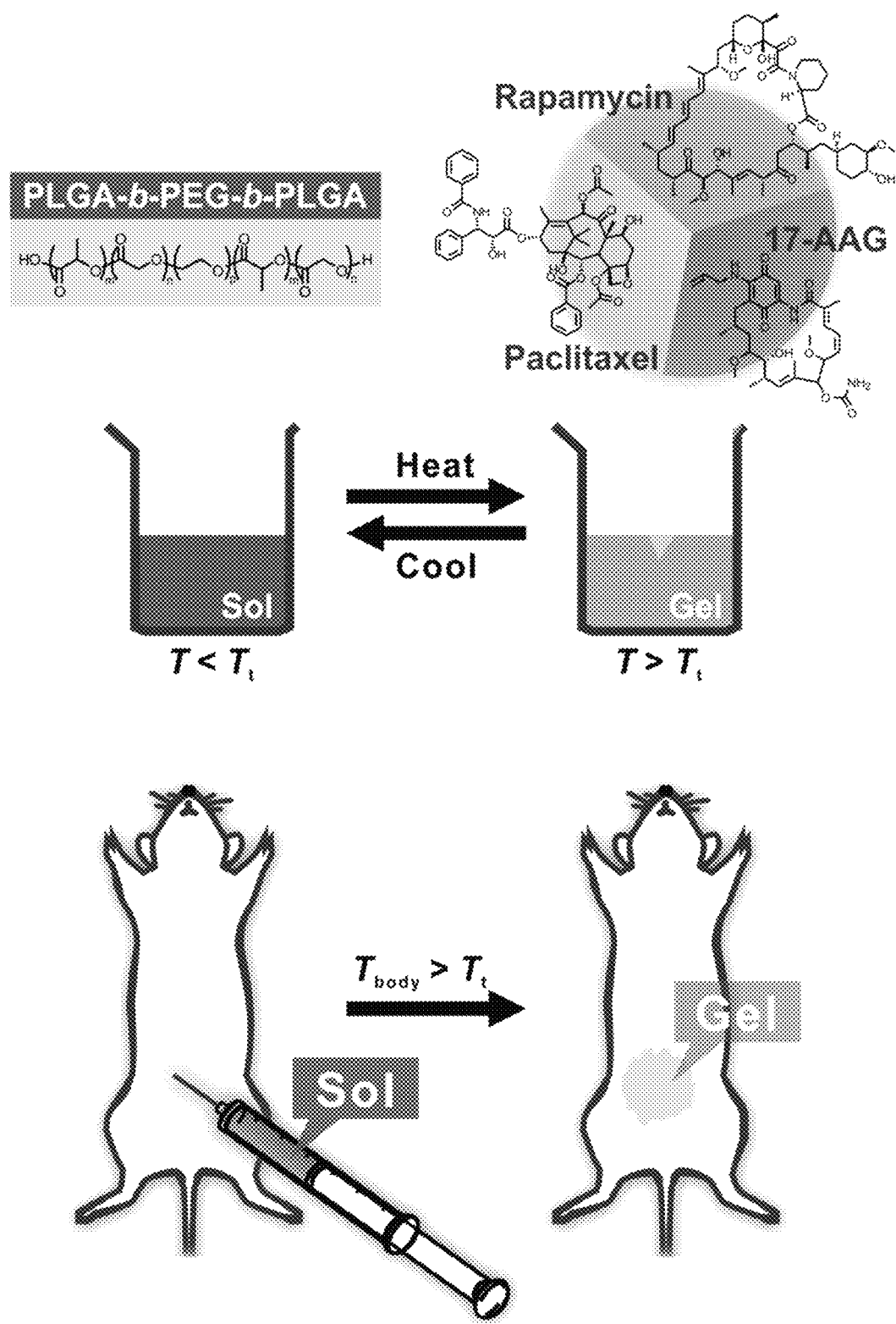
FIG. 1. A schematic for combination drug delivery via a PLGA-PEG-PLGA thermogel, where the thermogel is a liquid at ambient temperature and forms a gel at mammalian body temperature.

Many hydrophobic drugs are of limited solubility and/or stability in conventional liquid carriers and are therefore difficult to formulate and administer to patients. In many cases, numerous administrations are required to achieve the desired therapeutic effect over an extended period of time. Long-term controlled delivery of such hydrophobic drugs is important to provide the practical applications of these medications. Another problem is patient compliance. It is often difficult to get a patient to follow a prescribed dosage regimen, particularly when the prescription is for a chronic disorder and the drug has acute side effects. Therefore, it would be highly desirable to provide a drug delivery system for the delivery of hydrophobic drugs at a controlled rate over a sustained period of time, without the above mentioned problems, in order to optimize the therapeutic efficacy, minimize the side effects and toxicity, and thereby increase efficacy and patient compliance.

Drug loaded polymeric devices and dosage forms have been investigated for long term treatment of various diseases. An important property of the polymer in such systems is biodegradability, meaning that the polymer can break down or degrade within the body to nontoxic components, either concomitant with the drug release or after all drugs has been released. Furthermore, techniques, procedures, solvents and other additives used to fabricate the device and load the drug should result in dosage forms that are safe for the patient and minimize irritation to surrounding tissue.

It is also important for a polymeric drug delivery system to be a compatible medium for a particular drug or drug combination. While many polymeric drug delivery systems are suitable for a wide variety of therapeutic agents, laboratory evaluation of the various polymer systems shows that their applicability to certain therapeutics, particularly hydrophobic drugs, is somewhat limited, and each drug and drug combination must be evaluated empirically for its compatibility with a particular system.

Many biodegradable implantable controlled release devices are fabricated from solid polymers such as polyglycolic acid, polylactic acid, or copolymers of glycolic and lactic acid. Due to the hydrophobic properties of these polymers, drug loading and device fabrication using these materials often requires organic solvents, for example, methylene chloride, chloroform, acetic acid or dimethyl formamide. Due to the toxic nature of some solvents, extensive drying is generally required. Described herein are new delivery systems that avoid the need for these toxic solvents, allow for the delivery of a combination of hydrophobic anticancer agents, and provide a substantially identical release rate of each agent in the combination.

DEFINITIONS

As used herein, the recited terms have the following meanings. All other terms and phrases used in this specification have their ordinary meanings as one of skill in the art would understand. Such ordinary meanings may be obtained by reference to technical dictionaries, such as *Hawley's*

*Condensed Chemical Dictionary* 14th Edition, by R. J. Lewis, John Wiley & Sons, New York, N.Y., 2001.

References in the specification to "one embodiment", "an embodiment", etc., indicate that the embodiment described may include a particular aspect, feature, structure, moiety, or characteristic, but not every embodiment necessarily includes that aspect, feature, structure, moiety, or characteristic. Moreover, such phrases may, but do not necessarily, refer to the same embodiment referred to in other portions of the specification. Further, when a particular aspect, feature, structure, moiety, or characteristic is described in connection with an embodiment, it is within the knowledge of one skilled in the art to affect or connect such aspect, feature, structure, moiety, or characteristic with other embodiments, whether or not explicitly described.

The singular forms "a," "an," and "the" include plural reference unless the context clearly dictates otherwise. Thus, for example, a reference to "a drug" includes a plurality of such drugs, so that a drug X includes a plurality of drugs X. It is further noted that the claims may be drafted to exclude any optional element. As such, this statement is intended to serve as antecedent basis for the use of exclusive terminology, such as "solely," "only," and the like, in connection with any element described herein, and/or the recitation of claim elements or use of "negative" limitations.

The term "and/or" means any one of the items, any combination of the items, or all of the items with which this term is associated. The phrase "one or more" is readily understood by one of skill in the art, particularly when read in context of its usage. For example, one or more active agents refers to one, one or two, one to three, two or three, or three or more.

The term "about" can refer to a variation of ±5%, ±10%, ±20%, or ±25% of the value specified. For example, "about 50" percent can in some embodiments carry a variation from 45 to 55 percent. For integer ranges, the term "about" can include one or two integers greater than and/or less than a recited integer at each end of the range. Unless indicated otherwise herein, the term "about" is intended to include values, e.g., weight percentages, proximate to the recited range that are equivalent in terms of the functionality of the individual ingredient, the composition, or the embodiment. The term about can also modify the end-points of a recited range as discuss above in this paragraph.

As will be understood by the skilled artisan, all numbers, including those expressing quantities of ingredients, properties such as molecular weight, reaction conditions, and so forth, are approximations and are understood as being optionally modified in all instances by the term "about." These values can vary depending upon the desired properties sought to be obtained by those skilled in the art utilizing the teachings of the descriptions herein. It is also understood that such values inherently contain variability necessarily resulting from the standard deviations found in their respective testing measurements.

As will be understood by one skilled in the art, for any and all purposes, particularly in terms of providing a written description, all ranges recited herein also encompass any and all possible sub-ranges and combinations of sub-ranges thereof, as well as the individual values making up the range, particularly integer values. A recited range (e.g., weight percentages or carbon groups) includes each specific value, integer, decimal, or identity within the range. Any listed range can be easily recognized as sufficiently describing and enabling the same range being broken down into at least equal halves, thirds, quarters, fifths, or tenths. As a non-limiting example, each range discussed herein can be readily broken down into a lower third, middle third and upper third, etc. As will also be understood by one skilled in the art, all language such as "up to", "at least", "greater than", "less than", "more than", "or more", and the like, include the number recited and such terms refer to ranges that can be subsequently broken down into sub-ranges as discussed above. In the same manner, all ratios recited herein also include all sub-ratios falling within the broader ratio. Accordingly, specific values recited for radicals, substituents, and ranges, are for illustration only; they do not exclude other defined values or other values within defined ranges for radicals and substituents.

One skilled in the art will also readily recognize that where members are grouped together in a common manner, such as in a Markush group, the invention encompasses not only the entire group listed as a whole, but each member of the group individually and all possible subgroups of the main group. Additionally, for all purposes, the invention encompasses not only the main group, but also the main group absent one or more of the group members. The invention therefore envisages the explicit exclusion of any one or more of members of a recited group. Accordingly, provisos may apply to any of the disclosed categories or embodiments whereby any one or more of the recited elements, species, or embodiments, may be excluded from such categories or embodiments, for example, for use in an explicit negative limitation.

The term "contacting" refers to the act of touching, making contact, or of bringing to immediate or close proximity, including at the cellular or molecular level, for example, to bring about a physiological reaction, a chemical reaction, or a physical change, e.g., in a solution, in a reaction mixture, in vitro, or in vivo.

The terms "inhibit", "inhibiting", and "inhibition" refer to the slowing, halting, or reversing the growth or progression of a disease, infection, condition, or group of cells. The inhibition can be greater than about 20%, 40%, 60%, 80%, 90%, 95%, or 99%, for example, compared to the growth or progression that occurs in the absence of the treatment or contacting, or compared to the growth or progression that occurs by treatment of a group of cells by a single drug composition.

The term "parenteral" refers to intramuscular, intraperitoneal, intra-abdominal, subcutaneous, and, to the extent feasible with a thermogel formulation, intravenous and intraarterial, for example, on a small scale.

"Gelation temperature" refers to the temperature at which a biodegradable block copolymer undergoes thermal gelation, i.e. the temperature below which the block copolymer is soluble in water and above which the block copolymer undergoes phase transition to increase in viscosity or to form a semi-solid gel. The terms "gelation temperature," "thermal gelation temperature," "reverse thermal gelation temperature," and similar terms can be used interchangeably, as would be readily recognized by one of skill in the art.

A "polymer solution", "aqueous solution" and the like, when used in reference to a biodegradable block copolymer contained in such solution, refers to a water-based solution having the recited block copolymer dissolved therein at a functional concentration, and maintained at a temperature below the gelation temperature of the block copolymer. "Thermal gelation" is the phenomena whereby a solution of a block copolymer spontaneously increases in viscosity, and in many instances transforms into a semisolid gel, as the temperature of the solution is increased above the gelation temperature of the copolymer. For example, the term "gel" includes both the semisolid gel state and the high viscosity state that exists above the gelation temperature. When cooled below the gelation temperature, the gel spontaneously reverses to reform the lower viscosity solution. Cycling between the solution and the gel may be repeated ad infinitum because the sol/gel transition does not involve any change in the chemical composition of the polymer system. Interactions to create the gel are physical in nature and do not involve the formation or breaking of covalent bonds.

A "drug delivery system" or "drug delivery composition having thermal gelation properties" refers to a polymer solution that contains a drug or combination of drugs, where the drug(s) per se can be either dissolved or colloidal), suitable for administration to a warm-blooded animal, which forms a gelled drug depot when the temperature is raised to or above the gelation temperature of the block copolymer.

A "depot" refers to a drug delivery system following administration to a warm-blooded animal, which has formed a gel upon the temperature being raised to or above the gelation temperature.

A "gel" refers to the semi-solid phase that spontaneously occurs as the temperature of the "polymer solution" or "drug delivery system" is raised to or above the gelation temperature of the block copolymer.

An "aqueous polymer composition" refers to either a drug delivery system or a gel comprised of the water phase having uniformly contained therein a drug or drug combination and the biodegradable block copolymer described herein. At temperatures below the gelation temperature the copolymer may be soluble in the water phase and the composition will be a solution. At temperatures at or above the gelation temperature the copolymer will solidify to form a gel with the water phase and the composition will be a gel or semi-solid.

The term "biodegradable" means that the block copolymer can chemically break down or degrade within the body to form nontoxic components under physiological conditions. The rate of degradation can be the same or different from the rate of drug release.

A "hydrophobic drug" refers to a water insoluble drug. A water insoluble drug has a solubility of less than 0.1 mg/mL in distilled water at 25° C. Within the context of this disclosure, a "slightly soluble drug" has a solubility of about 1-10 mg/mL and a "very slightly soluble drug" has a solubility of about 0.1-1 mg/mL. These terms are well-known to those of skill in the art. See, e.g., Martin (ed.), *Physical Pharmacy*, Fourth Edition, page 213 (Lea and Febiger 1993). When hydrophobic drugs can be successfully used to prepare stable thermogels formulations, they can be extruded through a 22-gauge needle at below their gelation temperature. Thus, these compositions can be suitable for non-invasive treatments using a hydrophobic drug or combination of hydrophobic drugs, as described herein.

A "stable thermogel," "thermogel," or "thermosensitive hydrogel" as used herein refers to a composition that forms a stable non-flowing hydrogel at above about 20° C. and is a free-flowing solution at less than about 10° C., wherein the hydrogel incorporates one or more therapeutic agents such as hydrophobic drugs.

"Molecular weight" as used herein in reference to polymers refers to number average molar mass or number average molecular weight ($M_n$), mass average molar mass or weight average molecular weight ($M_w$), viscosity average molar mass ($M_v$), and/or Z average molar mass ($M_z$).

Thermogel Polymers

"Poly(lactide-co-glycolide)" or "PLGA" refers to a copolymer derived from the condensation copolymerization of lactic acid and glycolic acid, or by the ring opening polymerization of α-hydroxy acid precursors, such as lactide or glycolide. The terms "lactide" and "lactate" and "glycolide" and "glycolate" can be used interchangeably.

ABA-type block copolymers, where the A-blocks are a relatively hydrophobic poly(lactide-co-glycolide) and the B-block is a relatively hydrophilic polyethylene glycol, having a hydrophobic content of about 50 to about 85% by weight and an overall block copolymer molecular weight of between about 3 kDa and 5 kDa can exhibit water solubility at low temperatures and undergo reversible thermal gelation at mammalian physiological body temperatures. At such high hydrophobic content it is unexpected that such block copolymers would be water soluble. It is generally taught that any polymer having a hydrophobic content in excess of 50% by weight is substantially insoluble in water and can only be made appreciably soluble in aqueous systems, if at all, when a certain amount of an organic cosolvent has been added.

However, useful thermogels can be prepared from the ABA-type block copolymers described herein. The polymers can be ABA-type block copolymers having hydrophobic PLGA A-block segments and hydrophilic PEG B-block segments of the formula:

PLGA-PEG-PLGA wherein the block copolymers that have utility as described herein, namely, compositional make-up within the indicated ranges that result in block copolymers that demonstrate the desired stable thermal gelling behavior. For purposes of molecular weight parameters, the molecular weight values are based on measurements by NMR or GPC (gel permeation chromatography) analytical techniques. The reported weight average molecular weights and number average molecular weights can be determined by GPC and NMR, respectively. The lactide/glycolide ratio can be calculated from NMR data. GPC analysis can be performed, for example, on a Styragel HR-3 column calibrated with PEG using RI detection and chloroform as the eluent. NMR spectra can be taken in $CDCl_3$.

In some embodiments, the PLGA-PEG-PLGA polymer can have a total molecular weight of about 3.1 kDa to about 4.5 kDa, a PEG content of about 15-50 wt. %, a total PLGA content of about 50-85 wt. %, a lactate content of about 60-85 mole percent, a glycolate content of about 15-40 mole percent, where the polymer is water soluble below the gelation temperature (e.g., about 10-20° C.) and forms a stable thermogel above the gelation temperature (e.g., above about 20° C.).

The biodegradable, hydrophobic A-block segments can be poly(α-hydroxy acids) derived or selected from the group of poly(D,L-lactide-co-glycolide) and poly(L-lactide-co-glycolide), referred to collectively as poly(lactide-co-glycolide). Assuming that the average molecular weight of each of the A-blocks in an ABA triblock copolymer is essentially the same, the average molecular weight (in daltons) of each poly(lactide-co-glycolide) polymeric A block (e.g., $PLGA_{1.5K}$) can be between about 1050 Da and about 1950 Da. For example, the average molecular weight of poly(lactide-co-glycolide) in the polymers may be from about 800 Da to about 1800 Da, from about 1000 Da to about 1700 Da, from about 1200 Da to about 1600 Da, or about 1400 Da to about 1500 Da. In some embodiments the average molecular weight may be about 800 Da, about 900 Da, about 1000 Da, about 1100, Da, about 1200 Da, about 1300 Da, about 1400 Da, about 1500 Da, about 1600 Da, about 1700 Da, or about 1800 Da, about 1900 Da, or ranges between any two of these values (including endpoints).

The hydrophobic A-blocks are used because of their biodegradable, biocompatible, and solubilization properties. The in vitro and in vivo degradation of these hydrophobic poly(lactide-co-glycolide) A-blocks is well understood and the degradation products are naturally occurring compounds that are readily metabolized and/or eliminated by the patient's body. PEG was chosen as the hydrophilic, water-soluble block because of its unique biocompatibility, non-toxicity, hydrophilicity, solubilization properties, and rapid clearance from a patient's body. The hydrophilic B-block can be formed from appropriate molecular weights of PEG. For example, the hydrophilic B-block segment can be polyethylene glycol (PEG) having an average molecular weight of about 600 to about 2200.

In one embodiment, the PLGA A-blocks are about 65 to 80% by weight of the copolymer and the PEG B-block are about 20% to about 35% by weight of the copolymer. Further, the overall average molecular weight of the entire ABA block copolymer can be about 3 kDa to about 5 kDa, about 3.5 kDa to about 4.5 kDa, or ranges between any two of these values (including endpoints).

The concentration at which the block copolymers are soluble at temperatures below the gelation temperature may be considered as the functional concentration. Block copolymer concentrations of as low as 3% and of up to about 50% by weight can be used and still be functional. However, concentrations in the range of about 5 to 40% are often suitable and concentrations in the range of about 10-30% by weight are particularly useful. To obtain a viable gel phase transition with the copolymer, a certain minimum concentration, e.g. about 3% by weight is required. At the lower functional concentration ranges the phase transition may result in the formation of a weak gel. At higher concentrations, a strong gel network is formed.

The biodegradable polyester block of the PLGA-PEG-PLGA polymer can be synthesized from a variety of monomers such as D,L-lactide, D-lactide, L-lactide, D,L-lactic acid, D-lactic acid, L-lactic acid, glycolide, glycolic acid, ε-caprolactone, 6-hydroxyhexanoic acid, γ-butyrolactone, 4-hydroxybutyric acid, δ-valerolactone, 5-hydroxyvaleric acid, hydroxybutyric acids, malic acid, and copolymers thereof. For purpose of illustration, the A-block copolymers are generally lactide or lactide-co-glycolide moieties. However, unless specifically referred to otherwise, the terms "lactide", "lactate", or "L" include all lactic acid derivatives and "glycolide", "glycolate", or "G" include all glycolic acid derivatives. In the hydrophobic polyester A-block, the molar ratio of lactate content to glycolate content (L:G ratio) can be about 3:1 and about 1:0, about 1:1 and about 1:0, or about 1:1 and about 1:0.1.

As used herein, polyethylene glycol (PEG) may also be referred to as poly(ethylene oxide) (PEO) or poly(oxyethylene). The average molecular weight (in daltons) of PEG in the polymers described herein may be about 700 Da to about 1300 Da. The average molecular weight of PEG in the polymers may be about 800 Da to about 2000 Da, about 900 Da to about 1500 Da, or about 1000 Da to about 1200 Da. In another embodiment the average molecular weight may be about 700 Da, about 800 Da, about 900 Da, about 1000 Da, about 1100, Da, about 1200 Da, about 1300 Da, about 1400 Da, about 1500 Da, about 1600 Da, about 1700 Da, about 1800 Da, about 1900 Da, about 2000 Da, or ranges between any two of these values (including endpoints).

Two or more different PLGA-PEG-PLGA polymers can be used to prepare a thermogel formulation, for example, the combinations described in U.S. Pat. No. 7,135,190 (Piao et al.). Mixing of two or more types of ABA or BAB triblock polyester polyethylene glycol copolymers can be done by mixing two or more individually synthesized triblock copolymers, or by synthesizing two or more tri-block copolymers in one reaction vessel. The mixture of copolymers resulting from these processes can have the same or different gelation properties. For example, a dual polymer system can be prepared with both polymers having polyester A blocks with the same lactide/glycolide ratio, molecular weight and polydispersity, and different B (PEG) block molecular weights.

The triblock copolymer can be synthesized by ring opening polymerization or condensation polymerization, for example, as described by U.S. Pat. No. 6,004,573 (Rathi et al.) and U.S. Pat. No. 7,135,190 (Piao et al.). Suitable polymers, such as PLGA-PEG-PLGA (1.5 k-1 k-1.5 k), can also be obtained commercially from suppliers such as Polyscitech (West Lafayette, Ind.; http://www.polyscitech.com).

Thermogels and Drug Solubilization

While some amphiphilic block copolymers can form stable theromgels having a polymer matrix that can solubilize certain types of cargo such as hydrophobic drugs, there is currently no standard for determining which polymers are best suited for solubilizing various types of therapeutic agents while maintaining gel stability. These determinations must still be made empirically because there is no way to accurately predict which polymers can successfully solubilize a particular material and concurrently maintain gel stability.

One useful ABA-type block copolymer is PLGA-PEG-PLGA. The polymer has been reported to be widely applicable to forming thermoogels for incorporation of a wide range of therapeutic agents. However, even this useful polymer has significant limitations. The polymer was unable to form a stable thermogel when mixed with the important immunosuppressant drug rapamycin. Under conditions that should result in the formation of a stable thermogel, upon warming the 4° C. solution of the polymer and rapamycin to 37° C., the composition remained non-viscous and did not form a stable gel.

Other hydrophobic drugs, including the anticancer drug cyclopamine and the pro-apoptotic agent gossypol, also prevented the formation of stable thermogel. When cyclopamine was combined with the PLGA-PEG-PLGA under conditions to provide a thermogel, only a free-flowing solution of the polymer composition resulted. When the temperature of a free-flowing solution of the polymer composition at 4° C. was raised to room temperature and above, only a cloudy non-viscous mixture resulted and a stable thermogel was unable to be prepared. Similar experimental results were obtained for the attempted preparation of a stable thermogel with gossypol. These experiments provide further evidence of the unpredictability of thermogel formation with hydrophobic drugs.

In spite of these failures, it was discovered that the PLGA-PEG-PLGA could in fact form stable thermogels with various drug combinations where each of the drugs of the stable thermogel at 37° C. has equivalent drug release kinetics.

The mixture of the biodegradable copolymer and drugs can be prepared as an aqueous solution of the copolymer below the gelation temperature to form a drug delivery system where the drugs can be either partially or completely dissolved, as described by the preparatory techniques described herein. When the drugs are partially dissolved, or, when the drug is essentially insoluble, the drug exists in a colloidal state such as a suspension or emulsion. This drug delivery system can then be administered parenterally, topically, transdermally or inserted into a cavity such as by ocular, vaginal, transurethral, rectal, nasal, oral, or aural administration to a patient whereupon it will undergo a reversible thermal gelation since body temperature will be above the gelation temperature.

A distinct advantage to the compositions described herein lies in the ability of the block copolymer to increase the solubility of many hydrophobic drugs. The combination of the hydrophobic A-blocks and hydrophilic B-block render the block copolymer amphiphilic in nature. The amphiphilic polymer therefore functions much as a soap or surfactant in having both hydrophilic and hydrophobic properties. This is particularly advantageous in the solubilization of hydrophobic or poorly water soluble drugs such as rapamycin and paclitaxel.

Another useful ABA-type block copolymer is PEG-PLGA-PEG. The triblock copolymer PEG-PLGA-PEG can be used in a variety of embodiments in place of the PLGA-PEG-PLGA described above. PEG-PLGA-PEG for use in thermogels can be prepared by procedures analogous to preparing PLGA-PEG-PLGA triblock copolymers, for example, as described by Jeong et al. (*Nature* (1997), 388:860-862; *J. Control. Release* (2000), 63:155-163; and *Adv. Drug Delivery Rev.* (2002), 54:37-51). The PEG-PLGA-PEG polymer exhibits sol-gel behavior over a concentration of about 5% w/w to about 40% w/w. Depending on the properties desired, the lactide/glycolide molar ratio in the PLGA copolymer can range from about 1:1 to about 20:1. The resulting copolymers are soluble in water and form a free-flowing liquid at room temperature, but form a hydrogel at mammalian body temperatures. PEG-PLGA-PEG triblock copolymer are also commercially available from manufactures such as Boehringer Ingelheim. One example is RESOMER RGP t50106, a PEG-PLGA-PEG triblock copolymer composed of a PLGA copolymer of 50:50 poly(DL-lactide-co-glycolide) and 10% w/w of PEG with a molecular weight of about 6000. The PLGA and PEG blocks can be varied as described herein for PLGA-PEG-PLGA triblock copolymers.

Another advantage to the composition described herein lies in the ability of the block copolymer to increase the chemical stability of many drug substances. Various mechanisms for degradation of drugs that lead to a drug's chemical instability can be inhibited when the drug is in the presence of the block copolymer. For example, paclitaxel can be substantially stabilized in the aqueous polymer composition relative to certain aqueous solutions of the same drug in the presence of organic co-solvents. This stabilization effect can be achieved with many other hydrophobic drugs, provided that a stable thermogel can be prepared with the particular drug or drug combination in combination with the chosen amphiphilic polymer.

In certain situations the drug loaded polymer may be administered in the gel state instead of as a solution. The gelation may be the result of raising the temperature of a drug laden polymer solution above the gelation temperature of the polymer prior to administration or caused by raising the concentration of the polymer in the solution above the saturation concentration at the temperature of administration. In either event, the gel thus formed may be administered parenterally, topically, transdermally or inserted into a cavity such as by ocular, vaginal, transurethral, rectal, nasal, oral, or aural administration.

In some instances, the functionality or physical stability of the polymers and hydrophobic drugs can be increased by various additives to aqueous solutions or suspensions of the drugs. Additives, such as polyols (including sugars), amino acids, surfactants, polymers, and certain salts may be used. These additives can be incorporated into the block copolymers which will then undergo the stable thermal gelation process upon warming to above the gelation temperature.

Thermogels for Localized Cancer Therapy

Thermosensitive polymer-based hydrogels (i.e., thermogels) have great potential in biomedical fields due to several advantages such as the convenience of application, biodegradable properties, sustained release of therapeutic agents, and region-specific activity. Thermosensitive PLGA-PEG-PLGA is a free flowing solution below ambient temperature but becomes a hydrogel at body temperature, thus forming a depot at the injection site and making it a promising vehicle for the local treatment for cancer (FIG. 1).

The invention provides a multidrug-loaded PLGA-PEG-PLGA triblock copolymer thermogel. In one embodiment, the triblock copolymer can be a $PLGA_{1.5K}$-$PEG_{1K}$-$PLGA_{1.5K}$ triblock copolymer, or a polymer where the molecular weights of the blocks are individually +/−10-30% from the aforementioned values. The multidrug-loaded thermogel can be used for the localized treatment of cancer. In one embodiment, the three-drug combination of paclitaxel (PTX), 17-AAG, and rapamycin (RAPA), referred to as Triogel, can be loaded into the thermogel at therapeutically effective levels. For example, the thermogel can be successfully loaded individual amounts and combinations of paclitaxel (PTX), 17-AAG, and rapamycin (RAPA) into a PLGA-PEG-PLGA thermogel, both individually and in combinations, depending on the particular drug. Furthermore, stable thermogels were prepared from the two-drug combinations of PTX/RAPA, PTX/17-AAG, RAPA/17-AAG, and 17-AAG/cyclopamine. Typical drug loading in the thermogels was about 1 mg drug per 10 mg polymer in the compositions, which formed clear and tight gels.

Most PLGA-PEG-PLGA thermogels containing 1-, 2-, or 3-drugs were physically stable at 4° C. as a solution and 37° C. as a gel. However, RAPA-loaded PLGA-PEG-PLGA thermogel lacked a gel-like integrity at 37° C. Regardless of combinations, successfully formed PLGA-PEG-PLGA thermogels containing drugs released their content at an equal rate. The estimation of time for 50% drug release ($t_{1/2}$) was approximately 10 hours, and the drug release curves reached a plateau at <60% within 48 hours. Because of the failure of the single-drug rapamycin composition to form a stable gel at 37° C., RAPA-loaded PLGA-PEG-PLGA thermogel showed a rapid release of RAPA with $t_{1/2}$<0.5 h. A summary of various gel formation experiments is provided in Table 1 below.

TABLE 1

Summary of Initial Gel Formation Experiments.

| Drug Composition | Drugs (mg) | Polymer (mg) | Thermogel Formation |
|---|---|---|---|
| Rapamycin (RAPA) | 3 or 6 | 30 or 60 | No |
| Cyclopamine (CYP) | 6 | 60 | No |
| Gossypol | 6 | 60 | No |
| Paclitaxel (PTX) | 6 | 60 | Yes |
| 17-AAG | 6 | 60 | Yes |
| PTX/RAPA | 6/3 | 90 | Yes |
| PTX/17-AAG | 6/6 | 120 | Yes |
| RAPA/17-AAG | 3/6 | 90 | Yes |
| CYP/17-AAG | 6/6 | 120 | Yes |
| PTX/17-AAG/RAPA | 6/6/3 | 150 | Yes |
| CYP/17-AAG/RAPA | 6/6/6 | 180 | Yes |

While each of rapamycin, cyclopamine, and gossypol prevented formation of a stable thermogel, paclitaxel alone and various combinations of hydrophobic drugs were successfully incorporated into a stable thermogel at 37° C. While some drug particles existed in the CYP/17-AAG/RAPA formulation, the gel remained a viscous at 37° C.

A remarkable aspect of the PLGA-PEG-PLGA thermogels is that the drugs had a similar loading capacity regardless of whether they were loaded singly or multiply. Additionally, regardless of combinations, the PLGA-PEG-PLGA thermogels containing drug(s) released their content at an equal rate. Furthermore, the three-drug combination of PTX, 17-AAG, and RAPA in a PLGA-PEG-PLGA thermogel synergistically inhibited proliferation of cancer cells, including ES-2 and SKOV-3 ovarian cancer cells. Because these drugs have related but distinct mechanisms of action, the ability to provide them in one drug delivery system locally, thereby avoiding systemic toxicity, will significantly aid the development of important new clinical therapies.

Another remarkable aspect of the is that the drug release profile of the drugs lacks any burst effect, in that the drug release follows an orderly release without in initial release of a large amount of actives followed by a reduced amount, followed by a gradually increasing amount of release of actives. Drug delivery systems often have burst effects, including many PLGA polymer delivery systems. The orderly release of the actives from the PLGA-PEG-PLGA thermogels described herein significantly aids the determination of therapeutically effective dosages in clinical studies.

The drug release from biodegradable polymer formulations is difficult to predict. Different drugs typically have different rates of release from the same polymer gel, including polymer gels comprising PLGA and PEG blocks (see Jeong et al., *J. Contr. Rel.* 2000, 63, 155-163). The thermogels described herein surprisingly provide equivalent rates of drug release for each drug in the two and three drug combinations, which can significantly aid clinical therapies by allowing for more accurate assessment and adjustment of dose levels in view of the synergistic anticancer efficacy of the formulations. The release rates of the drugs remain comparable to each other over extended periods of time, including for more than two days.

The invention thus provides a novel three-drug thermogel for local cancer treatment that is more effective than the Oncogel® paclitaxel formulation. The two-drug thermogels described herein can also be more effective than the Oncogel® paclitaxel formulation. Additionally, the invention provides effective methods for preparing thermogels containing various combinations of paclitaxel, 17-AAG, and rapamycin. The invention thus provides a novel drug delivery system for the local treatment of cancer, including cancers such as brain, esophagus, head and neck, pancreatic, ovarian, and lymph node metastasis in breast cancer, using the combination of paclitaxel, 17-AAG, and rapamycin.

Therapeutic Agents

Paclitaxel Compounds.

Paclitaxel is a mitotic inhibitor and known chemotherapeutic agent, the structure of which is illustrated in FIG. 1. Paclitaxel can trigger apoptosis and inhibit mitotic spindle assembly and cell division. Paclitaxel derivatives or analogs may be exchanged with paclitaxel in the formulations herein. Such derivatives and analogs include docetaxel, 7-hexanoyltaxol (QP2), 3'-desphenyl-3'-(4-ntirophenyl)-N-dibenzoyl-N-(t-butoxycarbonyl)-10-deacetyltaxol, and other known paclitaxel derivatives. Several paclitaxel derivatives are known in the art and are disclosed in, for example, U.S. Pat. No. 5,399,726 (Holton et al.); U.S. Pat. No. 5,470,866 (Kingston et al.); U.S. Pat. No. 5,654,447 (Holton et al.); U.S. Pat. No. 6,107,332 (Ali et al.); U.S. Pat. No. 6,118,011 (Mayhew et al.); and U.S. Pat. No. 6,136,961 (Dordick et al.).

17-AAG Compounds.

Geldanamycin is a natural product inhibitor of Heat Shock Protein 90 (Hsp90), obtainable by culturing *Streptomyces hygroscopicus* var. *geldanus* NRRL 3602. Hsp90 is an important target for cancer therapy due to its key role in regulating proteins that are involved in tumor cell proliferation. It was discovered that geldanamycin, a benzoquinone ansamycin antibiotic, strongly binds to the ATP/ADP binding pocket of Hsp90, interfering with the survival and growth of a diverse family of tumors, including HER-2/erbB-2 overexpressing, paclitaxel resistant breast cancers. Clinical development of geldanamycin has been hampered by its poor solubility and severe hepatotoxicity (Ge et al., *J. Med. Chem.* 49(15) (2006) 4606-4615).

The geldanamycin analogues 17-allylamino-17-demethoxygeldanamycin (17-AAG; tanespimycin, FIG. 1) and 17-dimethylamino-ethylamino-17-demethoxygeldanamycin (17-DMAG, alvespimycin) were developed in part to improve the water solubility of geldanamycin. These compounds can be used in place of or in addition to the 17-AAG of the stable thermogels described herein. Additional 17-AAG compounds include 17-hydroxy-ethylamino-17-demethoxygeldanamycin, 17-amionoethyl-hexonate-17-demethoxygeldanamycin, 17-amionoethyl-bromohexonate-17-demethoxygeldanamycin, 17-aminoethyl-dodeconate-17-demethoxygeldanamycin, 17-aminoethyl-bromododeconate-17-demethoxygeldanamycin, 17-amionoethyl-palmitate-17-demethoxygeldanamycin, 17-aminoethyl-bromopalmitate-17-demethoxygeldanamycin, 17-amiono-hexyldecyl-17-demethoxygeldanamycin, which are described by U.S. Patent Publication No. 2006/0251710 (Kwon et al.). Other analogs include the compounds described in U.S. Patent Publication Nos. 2005/0101656 (Tian et al.), 2007/0270396 (Santi et al.), and 2006/0019941 (Adams et al.). Each of these compounds is considered a 17-AAG compound, as used herein, which can be used to form a stable thermogel using the methods described herein.

The compound 17-AAG is also a promising heat shock protein 90 inhibitor currently undergoing clinical trials for the treatment of cancer. Despite its selective mechanism of action on cancer cells, 17-AAG faces challenging issues due to its poor aqueous solubility. Suitable water solubility is of particular importance for parenteral administration. The water solubility of 17-AAG is only about 0.1 mg/mL at neutral pH, making it difficult to administer in a safe and effective manner. Attempts have been made to address the solubility issue but each formulation was accompanied by its own drawbacks, such as the use of DMSO, ethanol, or various undesirable surfactants.

Current 17-AAG compositions require formulation with Cremophor® EL (CrEL), DMSO, and/or ethanol (see U.S. Application Publication No. 2005/0256097 (Zhong et al.)). The use of CrEL is undesirable from a patient tolerability standpoint because CrEL is known to induce hypersensitivity reactions and anaphylaxis, and requires patient treatment with antihistamines and steroids before administration. Accordingly, safer and more effective delivery of 17-AAG compounds relies on the development of biocompatible delivery systems capable of solubilizing the drug without the use of harsh surfactants, such as the thermogel formulations described herein.

Rapamycin Compounds.

Rapamycin is a macrolide produced by *Streptomyces hygroscopicus* and discovered in the 1970s. See FIG. 1. Rapamycin is a potent immunosuppressive agent and is used clinically to prevent rejection of transplanted organs. It has also been reported to have a wide range of interesting pharmacologic activities, including certain anti-cancer activity. See for example, U.S. Patent Publication No. 2001/0010920 (Molnar-Kimber et al.). A number of derivatives of rapamycin, including AP23573 (ARIAD), CCI779 ("temsirolimus", Wyeth) and RAD001 ("Everolimus", Novartis) have yielded promising results in human studies against a variety of cancers. In addition, rapamycin and everolimus are used as immunosuppressants in organ transplant recipients. Rapamycin and a number of the C-43-modified rapamycin analogs, including among others AP23573, Biolimus and ABT-578 (Abbott), are being used, evaluated or developed for use on drug-eluting stents. Further derivatives of rapamycin are described in U.S. Patent Publication No. 2008/0207644 (Sonis et al.). Additional examples of rapamycin derivatives are described by U.S. Pat. No. 7,091,213 (Metcalf III et al.) (e.g., AP23573), WO 2004/026280, WO 2005/011688, WO 2005/070393, WO 2006/086172 and WO 2006/089312 (e.g., temserolimus (CCI779)), U.S. Pat. Nos. 6,384,046, 6,197,781, 6,004,973, WO 2002/066019 (e.g., for everolimus), 42-desmethoxy derivatives of rapamycin and its various analogs, as disclosed, e.g., in WO 2006/095185 (in which such compounds are referred to as "39-desmethoxy" compounds based on their numbering system), and references cited in such documents.

Combination Drug Therapy.

Combination drug therapy is becoming increasingly important for the treatment of cancer. Researchers are interested in the combination of chemotherapy and signal transduction inhibitors, as well as the combination of different signal transduction inhibitors. Combination cancer therapy is desirable for patients because of various benefits over monotherapy, including slower/less development of drug resistance and synergistic cancer cell-killing effects.

The importance of multi-drug thermogels is underscored by the shift in chemotherapy practices to combination drug therapy. This shift has been hampered by the differing solubilities of the therapeutics and different modes of delivery. Combining two or three drugs is often problematic in clinical practice because of solubility, compatibility and stability issues.

In murine tumor models and in early clinical trials, the chemotherapeutic paclitaxel has been shown to act synergistically with 17-AAG, a signal transduction inhibitor. However, paclitaxel and 17-AAG are difficult to solubilize, thus effective drug delivery systems are needed for clinical development of drug combination therapy.

Each of paclitaxel, 17-AAG, and rapamycin are poorly water-soluble, requiring specialized vehicles for drug solubilization, administration, and delivery. These current drug vehicles also have to be infused separately into patients via sequential drug administration in a single catheter line, increasing time of administration, or via concurrent drug administration in multiple catheter lines, raising risks of infection and adverse drug interactions. Existing vehicles for drug solubilization often include toxic components, such as CrEL. However, the thermogels described herein, prepared from biocompatible PLGA-PEG-PLGA polymers, can solubilize these active agents together in the same drug delivery system. These formulations offer a new approach for the delivery of a triple drug combination for the inhibition of cancer cell growth and for the treatment of cancer. The multidrug compositions described herein provide significant advantages to other treatments because lower amounts of one drug can be administered with equivalent or enhanced effect, while also, for example, inhibiting heat shock protein 90 and anti-apoptotic proteins. Accordingly, various one, two, and three drug combination formulations can be prepared, where the drugs are dissolved in the polymer matrix of the thermogel.

Thermogel Preparation

For poorly water-soluble drugs such as paclitaxel, rapamycin, 17-AAG, and cyclopamine, various methods were attempted to prepare stable thermogel. Standard solvent evaporation methods and nano-precipitation methods failed to provide suitably stable thermogels containing combinations of these active agents. However, a new procedure was developed that enabled the preparation of stable thermogels.

Drug delivery system containing a combination of three drugs can be prepared by dissolving the actives in a suitable alcoholic solvent system (e.g., about 1 mg to about 1.5 mg per 0.1 mL of solvent), such as tert-butanol or a tert-butanol/water solution to form a translucent solution. Heating the actives and the solvent system, such as to about 50-60° C., can aid in dissolving the actives. For example, 6, 6, and 3 mg of paclitaxel, 17-AAG, and rapamycin, respectively, can be dissolved in about 1 mL of tert-butanol at about 60° C. The polymer matrix can be prepared by dissolving a PLGA-PEG-PLGA polymer in cold water. The aqueous polymer solution can be incubated at refrigeration temperature (e.g., about 4° C.) for a period of time sufficient to provide a solution of the polymer. For example, $PLGA_{1,500}$-$PEG_{1,000}$-$PLGA_{1,500}$ triblock copolymer can be dissolved in water at about 4° C. The polymer solution can then be rapidly added to the drug/alcoholic solvent solution. The mixture can be vortexed and warmed to 50-60° C. for briefly to prevent phase separation. The mixture can then be rapidly frozen with ethanol/dry ice (−72° C.) and lyophilized to provide a cake or powder of the dehydrated formulation. Cold water (~4° C.) can be added to the lyophilized sample to provide a clear solution of the drug delivery system. The rehydrated solution can optionally be incubated at about 4° C. for 30 minutes prior to filtering the solution with a regenerated cellulose filter to remove drugs unincorporated in the thermogel. The thermogel can then be diluted with cold acetonitrile and the content of drugs incorporated can be quantified using Reverse Phase HPLC (RP-HPLC) analysis.

Triolimus Preparation

Drug delivery system containing a combination of three drugs can be prepared by dissolving 150 mg of PEG-b-PLA and 6 mg of paclitaxel, 6 mg of 17-AAG, and 3 mg of rapamycin in 2 mL of acetonitrile. The acetonitrile can then be removed by reduced pressure using rotary evaporator at 60° C. to produce a thin film consisting of a mixture of polymer and the three drugs. The mixture can then be rehydrated with 1 mL of pre-warmed distilled water at 60° C. to produce the final concentrations of 6, 6, and 3 mg/mL of paclitaxel, 17-AAG, and rapamycin, respectively. The aqueous solution can then be centrifuged and passed through 0.22 μm regenerated cellulose (RC) filter to remove unincorporated drugs. The content of drugs incorporated can then be quantified using Reverse Phase HPLC (RP-HPLC) analysis.

Therapy Using Thermogel Formulations

The lack of suitable formulations has hindered the progression of therapeutic agents such as rapamycin, paclitaxel, 17-AAG, and cyclopamine into clinical trials. Thermogel formulations of rapamycin, paclitaxel, 17-AAG, and/or cyclopamine that do not require organic co-solvents or harsh surfactants have been developed, as described herein. The formulations can solubilize significant amounts of each drug, on the order of 1-10 mg/mL of the drug delivery system depot.

The invention thus provides methods for inhibiting the growth of cancer cells or killing cancer cells comprising contacting the cancer cells or a cancer tumor with an effective inhibitory or lethal amount of a composition or formulation as described herein. The contacting can be in vivo or in vitro.

The invention also provides a method of treating a hyperproliferative disease in a subject comprising administering to a subject in need of such treatment a therapeutically effective dose of a composition or formulation as described herein and optionally one or more additional active agents, the method used optionally in combination with radiation, heat, or both, wherein the hyperproliferative disease is thereby treated. The hyperproliferative disease (e.g., a cancer or a neoplastic disease) can be associated with overexpression of a Bcl-2 family member protein. The Bcl-2 family protein can be, for example, Bcl-2, Bcl-$X_L$, Mcl-1, A1/BFL-1, BOO-DIVA, Bcl-w, Bcl-6, Bcl-8, or Bcl-y.

The invention further provides a method of simultaneously administering two or three drugs to a patient that has, or has been diagnosed with, cancer that can be treated by administration of at least one of a rapamycin compound, a paclitaxel compound, a 17-AAG compound, or a cyclopamine compound. The method can include administering an effective amount of a composition or formulation as described herein; wherein the cancer is thereby treated.

The cancer or the cancer cells can include, for example, brain tumor cells, breast cancer cells, colon cancer cells, head and neck cancer cells, lung cancer cells (SCLC or NSCLC), lymphoma cells, melanoma cells, neuroblastoma cells, ovarian cancer cells, pancreatic cancer cells, prostate cancer cells, or leukemia cells.

Various diseases, disorders, and conditions can be treated by administering a thermogel pharmaceutical formulation described herein. Administration of these compositions can result in a reduction in the size and/or the number of cancerous growths in a patient, and/or a reduction in one or more corresponding associated symptoms. When administered in an effective amount, the compositions can produce a pathologically relevant response, such as inhibition of cancer cell proliferation, reduction in the size of a cancer or tumor, prevention of further metastasis, inhibition of tumor angiogenesis, and/or death of cancerous cells. The method of treating such diseases and conditions described herein includes administering a therapeutically effective amount of a composition of the invention to a patient. The method may be repeated as necessary, for example, daily, weekly, or monthly, or multiples thereof.

Conditions that can be treated include, but are not limited to, hyperproliferative diseases, including cancers of the head and neck, which include tumors of the head, neck, nasal cavity, paranasal sinuses, nasopharynx, oral cavity, oropharynx, larynx, hypopharynx, salivary glands, and paragangliomas; cancers of the liver and biliary tree, particularly hepatocellular carcinoma; intestinal cancers, particularly colorectal cancer; ovarian cancer; small cell and non-small cell lung cancer; prostate cancer; pancreatic cancer; breast cancer sarcomas, such as fibrosarcoma, malignant fibrous histiocytoma, embryonal rhabdomyosarcoma, leiomysosarcoma, neurofibrosarcoma, osteosarcoma, synovial sarcoma, liposarcoma, and alveolar soft part sarcoma; neoplasms of the central nervous systems, particularly brain cancer; and/or lymphomas such as Hodgkin's lymphoma, lymphoplasmacytoid lymphoma, follicular lymphoma, mucosa-associated lymphoid tissue lymphoma, mantle cell lymphoma, B-lineage large cell lymphoma, Burkitt's lymphoma, or T-cell anaplastic large cell lymphoma. The drug delivery systems are particularly useful for the localized treatment of a tumor, such as a solid tumor.

The terms "treat", "treating", and "treatment" refer to any process, action, application, therapy, or the like, wherein a mammal, including a human being, is subject to medical aid with the object of improving the mammal's condition, directly or indirectly. Treatment can refer to the administration of an effective amount of a thermogel composition as described herein. Treatment can include (i) preventing a disease, pathologic or medical condition from occurring (e.g., prophylaxis); (ii) inhibiting the disease, pathologic or medical condition or arresting its development; (iii) relieving the disease, pathologic or medical condition; and/or (iv) diminishing symptoms associated with the disease, pathologic or medical condition. Thus, the terms "treat", "treatment", and "treating" can in some cases extend to prophylaxis and include prevent, prevention, preventing, lowering, stopping or reversing the progression or severity of the condition or symptoms being treated. As such, the term "treatment" includes medical, therapeutic, and/or prophylactic administration, in some embodiments.

The terms "effective amount" or "therapeutically effective amount" qualify the amount of a therapeutic agent that is effective to relieve to some extent one or more of the symptoms of a condition, disease or disorder, including, but not limited to: 1) reducing the number of cancer cells; 2) reducing tumor size; 3) inhibiting (i.e., slowing to some extent, preferably stopping) cancer cell infiltration into peripheral organs; 3) inhibiting (i.e., slowing to some extent, preferably stopping) tumor metastasis; 4) inhibiting, to some extent, tumor growth; 5) relieving or reducing to some extent one or more of the symptoms associated with the disorder; and/or 6) relieving or reducing the side effects associated with the administration of active agents.

Thus, an effective amount refers to an amount effective to treat a disease, disorder, and/or condition, or to bring about a recited effect. For example, an amount effective can be an amount effective to reduce the progression or severity of the condition or symptoms being treated. Determination of a therapeutically effective amount is well within the capacity of persons skilled in the art. The term "effective amount" is intended to include an amount of a therapeutic agent or thermogel composition described herein, e.g., that is effective to treat or prevent a disease or disorder, or to treat the symptoms of the disease or disorder, in a host. Thus, an effective amount generally means an amount that provides the desired effect.

The term "inhibition," in the context of neoplasia, tumor growth or tumor cell growth, may be assessed by delayed appearance of primary or secondary tumors, slowed development of primary or secondary tumors, decreased occurrence of primary or secondary tumors, slowed or decreased severity of secondary effects of disease, arrested tumor growth and regression of tumors, among others. In the extreme, complete inhibition can be referred to as prevention or chemoprevention. The inhibition can be about 10%, about 25%, about 50%, about 75%, or about 90% inhibition, with respect to progression that would occur in the absence of treatment or contact.

This system will cause minimal toxicity and minimal mechanical irritation to the surrounding tissue due to the biocompatibility of the materials and pliability of the gel, and will completely biodegrade to lactic acid, glycolic acid, and PEG within a specific time interval. The drug release, gel strength, gelation temperature and degradation rate can be controlled by proper design and preparation of the various copolymer blocks, namely, through modifications of the weight percent of the A-blocks and B-block, the mole percentages of lactate and glycolate, and the molecular weight and polydispersity of the ABA triblock copolymer. Drug release is also controllable through adjustment of the concentration of polymer in the drug delivery system.

A dosage form comprised of a solution of the block copolymer that contains either dissolved drugs or drugs as a suspension or emulsion can be administered to the body. This formulation then spontaneously gels due to the thermosensitive gelation properties of the block copolymer to form a drug depot as the temperature of the formulation rises to body temperature. The only limitation as to how much drug can be loaded into the formulation is one of functionality, namely, the drug load may be increased until the thermal gelation properties of the copolymer are adversely affected to an unacceptable degree, or until the properties of the formulation are adversely affected to such a degree to make administration of the formulation unacceptably difficult. Generally, in most instances the drug will make up between about 0.01 to 20% by weight of the thermogel formulation, typically with ranges of about 0.01 to 10%. Drug loading outside of these ranges can also be achieved.

Using a pharmaceutical formulation of this invention, active agents such as rapamycin, paclitaxel, and 17-AAG and/or other anticancer or cytotoxic agent may be administered in a dose ranging from about 4 mg/m$^2$ to about 4000 mg/m$^2$, depending on the frequency of administration. In one embodiment, a dosage regimen for the drug combinations can be about 400-500 mg/m$^2$ weekly, or about 450 mg/m$^2$ weekly. See Banerji et al., *Proc. Am. Soc. Clin. Oncol.*, 22, 199 (2003, abstract 797). Alternatively, a dose of about 300 mg/m$^2$ to about 325 mg/m$^2$, or about 308 mg/m$^2$ weekly can be administered to the patient. See Goetz et al., *Eur. J. Cancer,* 38 (Supp. 7), S54-S55 (2002). Another dosage regimen includes twice weekly injections, with doses ranging from about 200 mg/m$^2$ to about 360 mg/m$^2$ (for example, about 200 mg/m$^2$, about 220 mg/m$^2$, about 240 mg/m$^2$, about 250 mg/m$^2$, about 260 mg/m$^2$, about 280 mg/m$^2$, about 300 mg/m$^2$, about 325 mg/m$^2$, 340 mg/m$^2$, about 350 mg/m$^2$, or about 360 mg/m$^2$, depending on the severity of the condition and health of the patient). A dosage regimen that can be used for combination treatments with another drug, such as paclitaxel or docetaxel, can administer the two drugs every three weeks, with the dose of 17-AAG of about 500 mg/m$^2$ to about 700 mg/m$^2$, or up to about 650 mg/m$^2$ at each administration. Other concurrent dosing schedules that can be employed are described by Fung et al., *Clin. Cancer Res.* 2009; 15(17), 5389-5395. Other dosing schedules, conditions that can be treated by the compositions described herein, and the like are described by WO 2011/025838 (Tao et al.)

Thus, the combination therapy disclosed herein encompasses methods of treating, preventing and/or managing various types of cancer while providing a desirable therapeutic window for achieving clinical benefit without incurring an unacceptable level of side effects.

Examples of cancers and cancer conditions that can be treated with the combination therapy of this document include, but are not limited to, solid tumors such as sarcomas and carcinomas, lymphatic cancers and phosphatase and tensin homolog (PTEN)-deficient tumors (see e.g. *PNAS* 98(18):10314-10325; Hidalgo et al, *Oncogene* (2000) 19, 6680-6686). PTEN-deficient tumors may be identified, using genotype analysis and/or in vitro culture and study of biopsied tumor samples. Non-limiting examples of cancers involving abnormalities in the phosphatidyl-inositol 3 kinase/Akt-mTOR pathway include, but are not limited to, glioma, lymphoma and tumors of the lung, bladder, ovary, endometrium, prostate or cervix which are associated with abnormal growth factor receptors (e.g., EGFR, PDGFR, IGF-R and IL-2); ovarian tumors which are associated with abnormalities in P13 kinase; melanoma and tumors of the breast, prostate or endometrium which are associated with abnormalities in PTEN; breast, gastric, ovarian, pancreatic, and prostate cancers associated with abnormalities with Akt; lymphoma, cancers of the breast or bladder and head and neck carcinoma associated with abnormalities in elF-4E; mantle cell lymphoma, breast cancer and head and neck carcinomas associated with abnormalities in Cyclin D; and familial melanoma and pancreas carcinomas associated with abnormalities in P16.

A "solid tumor" refers to a tumor and/or metastasis, such as a brain and other nervous system tumor (e.g. a tumor of the meninges, brain such as glioblastoma and astrocytomas, spinal cord and other parts of the central nervous system); head and/or neck cancer; breast tumors; excretory system tumors (e.g. kidney, renal, pelvis, bladder and other unspecified organs); gastrointestinal tract tumors (e.g. oesophagus, stomach, colon, small intestine, rectum, tumors involving the liver, gall bladder, pancreas and other parts of the digestive organs); oral cavity (lips, tongue, throat, mouth, tonsil, oropharynx, nasopharynx, and other sites); reproductive system tumors (e.g. vulva, cervix, uterus, ovary and other sites associated with female genital organs, penis, prostate, testis and other sites associated with male genital organs); respiratory tract tumors (e.g. nasal cavity, middle ear, sinuses, bronchus, lung and other sites); skeletal system tumors (e.g. bones, cartilage and other sites); skin tumors (e.g. malignant melanoma of the skin, non-melanoma skin cancer, carcinoma, sarcoma); and tumors involving other tissues including peripheral nerves, connective and soft tissue, eye and adnexa, thyroid, adrenal gland and other endocrine glands and related structures, secondary and unspecified malignant neoplasm of lymph nodes, secondary malignant neoplasm of respiratory and digestive systems and secondary malignant neoplasm of other sites.

A "lymphatic cancer" refers to a tumor of the blood and lymphatic system (multiple myeloma, lymphoid leukemia, myeloid leukemia, acute or chronic lymphocytic leukemia, monocytic leukemia, other leukemias of specified cell type, leukemia of unspecified cell type, other unspecified malignant neoplasms of lymphoid, haematopoietic and related tissues, for example T-cell lymphoma or cutaneous lymphoma).

Cancers that can be treated using this combination therapy include cases that are refractory to treatment with other chemotherapeutics. The term "refractory" refers to a cancer (and/or metastases thereof) that shows no or only weak anti-proliferative response (e.g., no or only weak inhibition of tumor growth) after treatment with another chemotherapeutic agent. These are cancers that cannot be treated satisfactorily with other chemotherapeutics. Refractory cancers encompass not only (i) cancers where one or more chemotherapeutics have already failed during treatment of a patient, but also (ii) cancers that can be shown to be refractory by other means, e.g., biopsy and culture in the presence of chemotherapeutics.

The thermogel formulations described herein can be used as degradable carriers for treating local diseases such as the cancer conditions described above. Site-specific chemotherapy that provides high drug concentrations for an extended time period at the diseased site is an effective way of treating remnant infected cells after resection of an infected area, such as a solid tumor. The formulation can be administered by injection and/or implantation, intramuscularly, subcutaneously, intraperitoneally, and/or intratumorally, for example, before, during or after tumor resection. The polymers are typically liquid or low viscosity pastes at below room temperatures such that they can be injected or implanted at an appropriate temperature, often without the need for additives. However, additives can be added to reduce the viscosity and/or improve the injectability of the compositions as needed.

In various embodiments, the thermogel formulations described herein can be used for site-specific chemotherapy for the treatment of solid tumors, including but not limited to: squamous cell carcinoma (SCC) of the head & neck, ovarian cancer pancreatic cancer, prostate cancer, and sarcomas, for example, for intratumoral injection or insertion.

Cancer of the head and neck accounts for about 40,000 new cases every year in the United States, which is about 5% of all new cancer cases in the country. Unlike other solid tumors, the most common manifestation of recurrence of head and neck cancer is regional (i.e., recurrence in the neck). A device based on the thermogels described herein can be a pasty or gel polymeric implant, made of a biodegradable polymer matrix loaded with a combination of anticancer agents as described herein. The anticancer agents can be homogeneously dispersed into the polymer matrix. The active drugs can be released in a controlled manner to the surrounding tissue, when placed in contact with body fluids, while the polymer carrier is eliminating by slow degradation.

The implant, in a form of an injectable liquid or paste, can be injected into the tumor or inserted into the tumor site, for example, during a surgical procedure of tumor removal. The implant can provide a high dose of a combination of anti-cancer drugs for an extended period of time, typically days, weeks or even months, at the tumor site, with minimal systemic drug distribution. Thus, the invention can provide a localized treatment of tumor cells, and/or residual tumor cells as a complementary drug therapy to the surgery. The compositions described herein can also be used as coatings on implantable medical devices, such as stents, as surgical sealants, or as barriers for the reduction of organ to organ adhesion.

Pharmaceutical Formulations

The thermogel compositions described herein can be formulated as pharmaceutical dosage forms and administered to a mammalian host, such as a human patient, by a variety of means. The route of administration can be parenteral administration, for example, by injection to provide a subcutaneous depot. Useful dosages of the compositions can be determined by comparing their in vitro activity, and in vivo activity in animal models. Methods for the extrapolation of effective dosages in mice, and other animals, to humans are known to the art; for example, see U.S. Pat. No. 4,938,949 (Borch et al.). Dosages can also be based on clinical evaluations described in the field, including those described by Elstad and Fowers, Adv. Drug Del. Rev. 2009, 61, 785-794. The amount of an active agent, or derivative thereof, for use in treatment will vary not only with the particular drug and drug combination selected but also with the route of administration, the nature of the condition being treated, and the age and condition of the patient, and will be ultimately at the discretion of an attendant physician or clinician.

The thermogel can be conveniently administered in a unit dosage form, for example, containing 5 to 1000 mg/m$^2$, conveniently 10 to 750 mg/m$^2$, most conveniently, 50 to 500 mg/m$^2$ of active ingredient, alone or in combination, per unit dosage form. The desired dose may conveniently be presented in a single dose or as divided doses administered at appropriate intervals, for example, as two, three, four or more sub-doses per week or per month. The sub-dose itself may be further divided, e.g., into a number of discrete loosely or evenly spaced administrations.

The thermogel compositions described herein are effective anti-tumor therapeutics and can provide higher potency and/or reduced toxicity compared to the Oncogel® paclitaxel formulation. Additionally, the multi-drug thermogels described herein can be more potent and less toxic than the Oncogel® paclitaxel formulation at lower dosage levels.

The invention thus provides therapeutic methods of treating cancer in a mammal, which involve administering to a mammal having cancer an effective amount of a composition described herein. A mammal includes a primate, human, rodent, canine, feline, bovine, ovine, equine, swine, caprine, bovine and the like. Cancer refers to any various type of malignant neoplasm, for example, colon cancer, breast cancer, melanoma, leukemia, and other forms of cancer as recited herein, and in general is characterized by an undesirable cellular proliferation, e.g., unregulated growth, lack of differentiation, local tissue invasion, and metastasis.

The ability of a thermogel composition to treat cancer may be determined by using assays well known to the art.

For example, the design of treatment protocols, toxicity evaluation, data analysis, quantification of tumor cell kill, and the biological significance of the use of transplantable tumor screens are known. In addition, ability of a compound to treat cancer may be determined using assays as described herein.

The following Examples are intended to illustrate the above invention and should not be construed as to narrow its scope. One skilled in the art will readily recognize that the Examples suggest many other ways in which the invention could be practiced. It should be understood that numerous variations and modifications may be made while remaining within the scope of the invention.

EXAMPLES

Example 1

Triogel Delivery System and Anticancer Therapy

A thermosensitive biodegradable hydrogel (i.e., thermogel) containing a three-drug combination has been developed. The composition is a free flowing solution at room temperature (~22° C.) and forms a hydrogel (depot) at body temperature (~37° C.). The thermogel provides a remarkably sustained release of each of the three drugs for a period of more than two days. The thermogel is particularly useful for localized drug delivery.

The drug delivery system containing a combination of three drugs can be prepared as follows. Paclitaxel (PTX; 6 mg), 17-AAG (6 mg), and rapamycin (RAPA; 3 mg) were combined with 1.5 mL of tent-Butanol (TBA) to obtain a clear solution at 60° C. Separately, cold water was added to $PLGA_{1.5k}$-$PEG_{1k}$-$PLGA_{1.5k}$ and the mixture was incubated at refrigeration temperature (4° C.) for 2-3 days to obtain 100 mg/mL of polymer solution. The polymer solution (1.5 mL) was rapidly added to 1.5 mL of drug/TBA mixture (50% TBA). The mixture was rapidly vortexed and warmed to 60° C. for less than one minute to prevent phase separation. The mixture was rapidly frozen with ethanol/dry ice (−72° C.) for 1 hour and lyophilized for 24 hours (below 0.8 bar at −45° C.). One mL of cold water (4° C.) was added to the lyophilized sample and the mixture was incubated in a refrigerator (4° C.) for about 113 days to obtain clear solution (x) of the drug delivery system and for less than about 3 days to obtain clear solution (y) of the drug delivery system.

At room temperature, gelation occurs in less than 2 minutes. Samples were diluted with cold water and kept at 4° C. Liquefied samples were passed through about 0.2 mm (e.g., clear solution (x)) to about 0.2 μm (e.g., clear solution (y)) of a regenerated cellulose membrane filter (RC filter) at 4° C. and concentrations were quantified using RP-HPLC.

The TBA fraction of the 6 mg/6 mg/3 mg sample of PTX/17-AAG/RAPA thermogel was 50%. Particle size of samples (before gelation) was observed using DLS at 4° C. Drug components (before gelation) were quantified using RP-HPLC while the sampler was kept at 4° C. The effect of the polymer level in the compositions is shown in Table 1-1. A polymer concentration of 150 mg/mL was found to be especially useful for use in a drug delivery vehicle.

TABLE 1-1

Effects of Polymer Levels.

| Polymer (mg/mL) | 30 | 50 | 80 | 100 | 150 |
|---|---|---|---|---|---|
| Z-average (nm) | 189.7 ± 2.0 | 188.9 ± 19.1 | 97.6 ± 2.8 | 86.5 ± 0.8 | 60.0 ± 0.2 |
| PDI | 0.3 ± 0.01 | 0.5 ± 0.03 | 0.4 ± 0.02 | 0.4 ± 0.01 | 0.3 ± 0.01 |
| Quantification (mg/mL) | 0.9/0.9/0.5 | 2.3/2.3/1.0 | 4.6/4.1/2.0 | 5.0/4.7/2.6 | 5.7/5.7/3.1 |

PDI: Polydispersity index (the distribution of particles in dynamic light scattering measurements (a PDI of less than 0.2 indicates that a sample is monodisperse).

The effect of TBA level in the composition was also evaluated. Data is shown below in Table 1-2. For a 6 mg/6 mg/3 mg sample of PTX/17-AAG/RAPA thermogel, 50% TBA was found to be especially useful for use in a drug delivery vehicle. Particle size of samples (before gelation) was observed using DLS at 4° C. Drug components (before gelation) were quantified using RP-HPLC while the sampler was kept at 4° C.

TABLE 1-2

Effects of TBA Levels.

| TBA (%) | 30 | 40 | 50 | 70 |
|---|---|---|---|---|
| Z-average (nm) | 107.3 ± 5.5 | 89.4 ± 2.2 | 60.6 ± 0.2 | 116.1 ± 3.3 |
| PDI | 0.3 ± 0.04 | 0.4 ± 0.01 | 0.3 ± 0.01 | 0.5 ± 0.06 |
| Quantification (mg/mL) | 5.6/5.3/2.5 | 5.6/5.2/2.5 | 5.7/5.7/3.1 | 5.1/5.2/2.7 |

Figure 2:
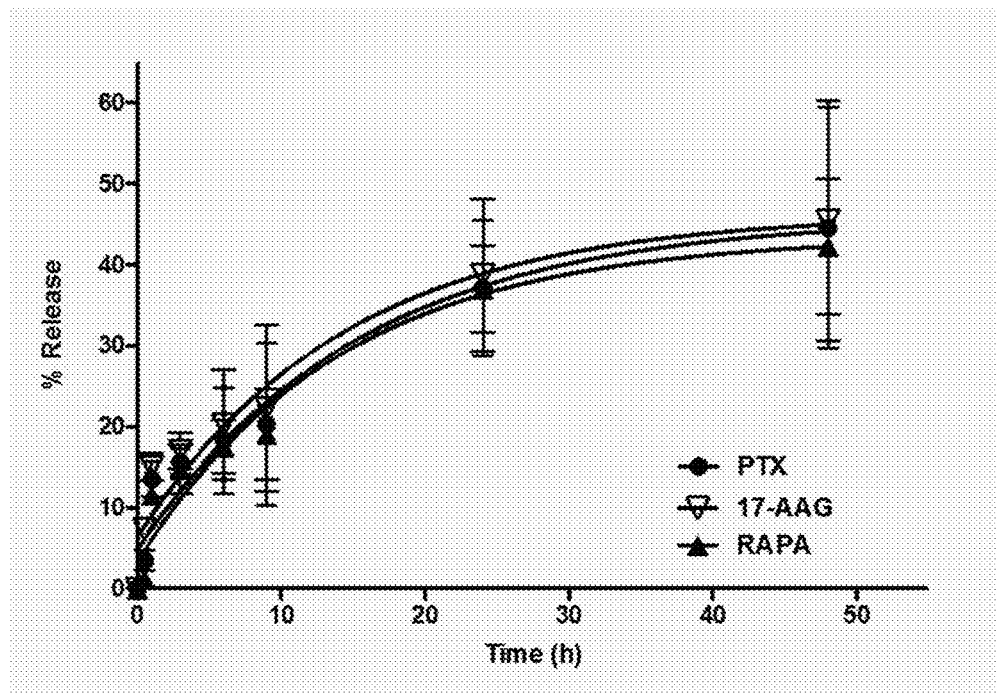
FIG. 2. Release kinetics at 37° C. of a Triogel formulation prepared from PTX/17-AAG/RAPA (6 mg, 6 mg, and 3 mg, respectively) and 150 mg of PLGA-PEG-PLGA in 1 mL of water.

The drug release kinetics of the composition at 37° C. was evaluated. Data is shown below in Table 1-3. A thermogel formed from a 6 mg/6 mg/3 mg combination of PTX/17-AAG/RAPA in 150 mg of polymer and 1 mL of water (a "Triogel" sample) was analyzed. Each cassette (MWCO 20,000) contained 0.3 mL of Triogel (n=3). Remarkably, each of the three drugs had a substantially similar release profile. The profile of the release kinetics was fit into a first-order model (Prism ver 5.0), as illustrated in FIG. 2.

TABLE 1-3

Drug Release Kinetics at 37° C.

| Drug (n = 3) | PTX | 17-AAG | RAPA |
|---|---|---|---|
| k | 0.0577 ± 0.0230 | 0.0770 ± 0.013 | 0.0900 ± 0.023 |
| $R^2$ | 0.9763 | 0.8911 | 0.9733 | k: release kinetic constant (h−1); higher constant represents faster release profile;.
R: goodness of fit, $R^2$ close to 1 indicates the best fit of the curves.

A summary of trials and conditions for a 6 mg/6 mg/3 mg combination of PTX/17-AAG/RAPA in 150 mg of $PLGA_{1.5k}$-$PEG_{1k}$-$PLGA_{1.5k}$ polymer in 50 wt. % TBA in water (a "Triogel" sample) is shown in Table 1-4.

TABLE 1-4

Summary of Trials and Conditions.

|  | Trial 1 | Trial 2 | Trial 3 | Trial 4 |
|---|---|---|---|---|
| Sucrose (mg/mL) | 0 | 135 | 135 | 270 |
| TBA (%) | 50 | 40 | 50 | 50 |
| Rehydration time (days) at 4° C. | 1 | >2 | >2 | >2 |
| Gelation time at RT (min) | <2 | <2 | <2 | <2 |

Solvent evaporation methods and nano-precipitation methods were also evaluated for the preparation of a three-drug thermogel. However, both types of methods failed to provide stable gels of the drug combinations.

Addition of a monosaccharide such as glucose or a disaccharide such as sucrose can provide favorable physical properties of the lyophilized compositions. Sucrose-containing lyophilized cakes had more favorable physical property (i.e., favorable cake-formation) compared to lyophilized formulations without sucrose formation, which formed gels. In general, an elegant lyophilized cake can improve rehydration time and solubility of the lyophilized cake in aqueous solution. The shape of lyophilized cake, however, did not affect the rehydration time and drug contents in the final product.

In vitro cytotoxicity of paclitaxel, 17-AAG, and rapamycin, individually and in combinations was evaluated in ES-2-luc human ovarian cancer cells and IC50 values of drug(s) dissolved in a mixture of DMSO and medium are summarized in Table 1-5. Individual treatment with rapamycin or 17-AAG did not induce significant cytotoxic effect in ES-2-luc cells, whereas a 2-drug combination of 17-AAG/rapamycin (2:1 w/w ratio) demonstrated a much lower $IC_{50}$ value of 343 nM, indicating a synergistic cell-killing effect. Paclitaxel alone and combinations of paclitaxel/rapamycin (1:1 molar ratio) resulted in comparably low $IC_{50}$ values at 125 and 112, respectively. The three-drug formulation (paclitaxel/17-AAG/rapamycin, 2:2:1 w/w/w ratio) synergistically inhibited proliferation of ovarian carcinoma cells, ES-2-luc (168 nM of $IC_{50}$) and SK-OV-3 (68 nM of $IC_{50}$), with combination indices (CI)<1. Accordingly, the thermogel formulation of two or more drugs provides a useful therapeutic drug delivery system for synergistically inhibiting the growth of cancer cells, and may be used to treat cancers that can be treated locally with a gel depot.

TABLE 1-5

$IC_{50}$ Values of Single, Two, and Three Thermogels.

| | Drug(s) | | | | | | |
|---|---|---|---|---|---|---|---|
| | PTX | 17-AAG | RAPA | PTX/ 17-AAG | PTX/ RAPA | RAPA/ 17-AAG | PTX/ 17-AAG/RAPA |
| $IC_{50}$ (nM) | 124.5 ± 25.2 | 933.6 ± 1.8 | >2.2 × $10^{11}$ | 518.8 ± 14.4 | 112.0 ± 11.3 | 342.9 ± 74.3 | 168.1 ± 37.2 |

TABLE 1-4-continued

Summary of Trials and Conditions.

|  | Trial 1 | Trial 2 | Trial 3 | Trial 4 |
|---|---|---|---|---|
| Final level of drug (mg/mL) | 5.7/5.7/3.1 | 4.6/4.4/2.0 | 5.5/5.9/3.2 | 4.0/4.5/2.6 |
| Physical observation of lyophilized sample | Gel-like | Porous | Cake | Cake |
| Physical observation of gel | Good | Good | Good | Good |

This example demonstrates that a thermosensitive PLGA-PEG-PLGA thermogel provides a high loading capacity for three-drug combinations of PTX, 17-AAG, and RAPA; undergoes successful sol-gel transition at body temperature; and shows equivalent rates of drug release for synergistic anticancer activity.

Example 2

Single and Two Drug Thermogel Delivery System

The procedures of Example 1 were used to prepare single drug and two drug thermogels. While the composition resulted in stable gels for several combinations, the gel was unable to be formed when incorporating only rapamycin into the polymer matrix. Analysis of the single drug and two drug evaluations are provided below in Table 2-1.

TABLE 2-1

Single and Two Drug Compositions.

| | Drugs | | | | | | |
|---|---|---|---|---|---|---|---|
| | PTX | 17-AAG | RAPA | PTX/ RAPA | PTX/ 17-AAG | RAPA/ 17-AAG | PTX/ 17-AAG/RAPA |
| Polymer (mg) | 60 | 60 | 60 | 60/30 | 60/60 | 30/60 | 60/60/30 |
| Initial level of drug (mg/mL) | 6.0 | 6.0 | 3.0 | 6.0/3.0 | 6.0/6.0 | 3.0/6.0 | 6.0/6.0/3.0 |

TABLE 2-1-continued

Single and Two Drug Compositions.

| | Drugs | | | | | | |
|---|---|---|---|---|---|---|---|
| | PTX | 17-AAG | RAPA | PTX/ RAPA | PTX/ 17-AAG | RAPA/ 17-AAG | PTX/ 17-AAG/RAPA |
| Final level of drug (mg/mL) | 5.8 ± 0.5 | 5.3 ± 0.3 | 1.6 ± 0.2 | 6.0/3.0 ± 0.5/0.2 | 5.6/5.5 ± 0.4/0.3 | 2.5/4.8 ± 0.2/0.4 | 5.7/5.7/3.1 ± 0.4/0.4/0.2 |
| Physical obs. of gel | Good | Good | Liquid-like | Good | Good | Good | Good |

Figure 3:
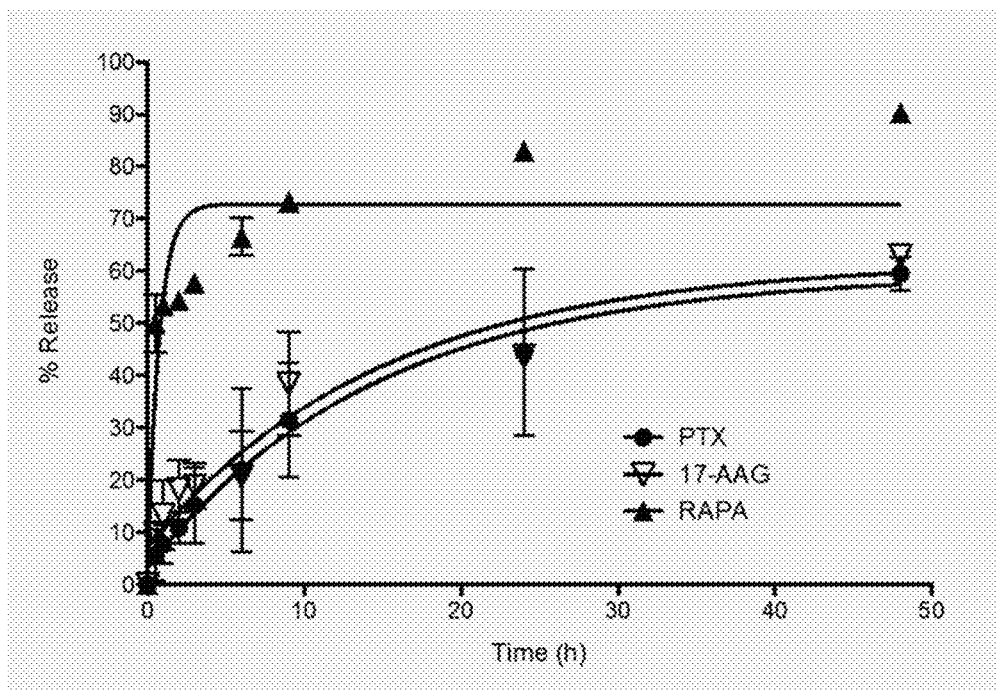
FIG. 3. Release kinetics at 37° C. of single drug formulations prepared with PLGA-PEG-PLGA, water, and the corresponding drug.

The release kinetics of 1-drug thermogels (37° C.) were analyzed. Separately, compositions having 6 mg, 6 mg, and 3 mg of PTX, 17-AAG, and RAPA mixed with 60, 60, and 30 mg of polymers, respectively, in 1.0 mL of water were evaluated. Each cassette (MWCO 20,000) contained 0.3 mL of Thermogel (n=3). Profile of release kinetics was fit into a first-order model (Prism ver 5.0). See Table 2-2 and FIG. 3.

TABLE 2-2

| Release Kinetics Data of Single Drug Compositions. | | | |
|---|---|---|---|
| Drug (n = 3) | PTX | 17-AAG | RAPA |
| k | 0.0682 ± 0.0112 | 0.06706 ± 0.0254 | 1.351 ± 0.6168 |
| $R^2$ | 0.9868 | 0.9341 | 0.8160 |

The single drug composition of polymer and rapamycin rapidly release drug from the polymer matrix due to a lack of gel-like matrix formation. More than 50% of the rapamycin of the sample was released within 0.5 hours, while the compositions that formed thermogels (e.g., paclitaxel and 17-AAG) typically retained more than 50% of the drug for approximately 30 hours. Additionally, when suitable thermogels were prepared with incorporation of a single drug, the resulting thermogels were stable for long periods of time. For example, a 6 mg PTX in 150 mg of polymer and 50 wt. % TBA sample (5.33 mg PTX gel incorporation by RP-HPLC analysis) formed a gel at room temperature in less than two minutes, and retained its gel-like form at room temperature for more than two weeks.

Figure 4A:
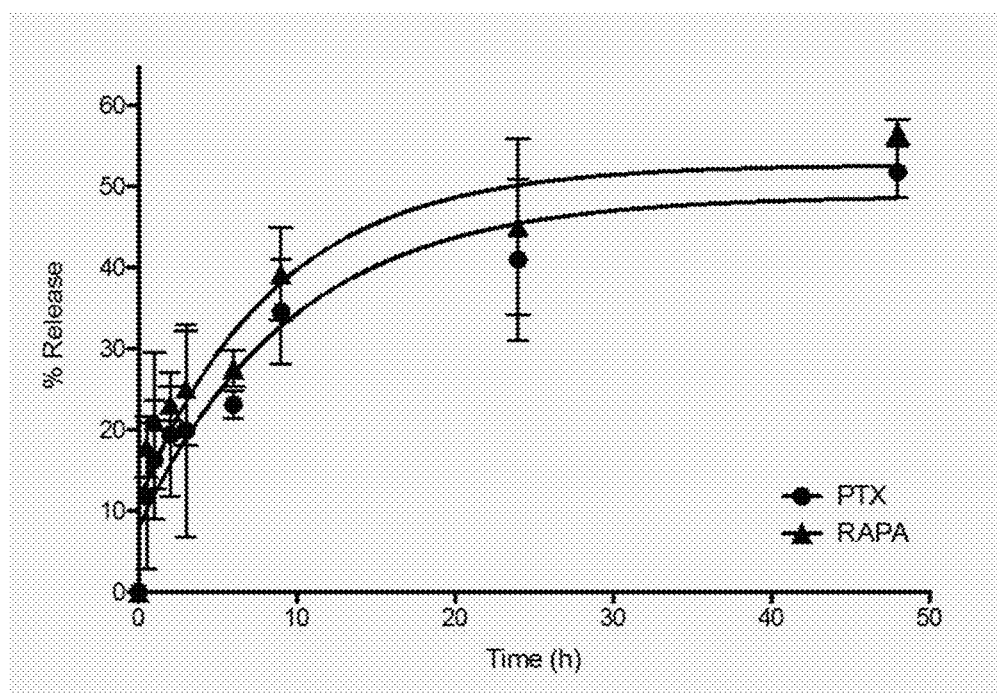
FIGS. 4A-C. Release kinetics at 37° C. of two drug formulations prepared with PLGA-PEG-PLGA, water, and the corresponding drugs.
Figure 4B:
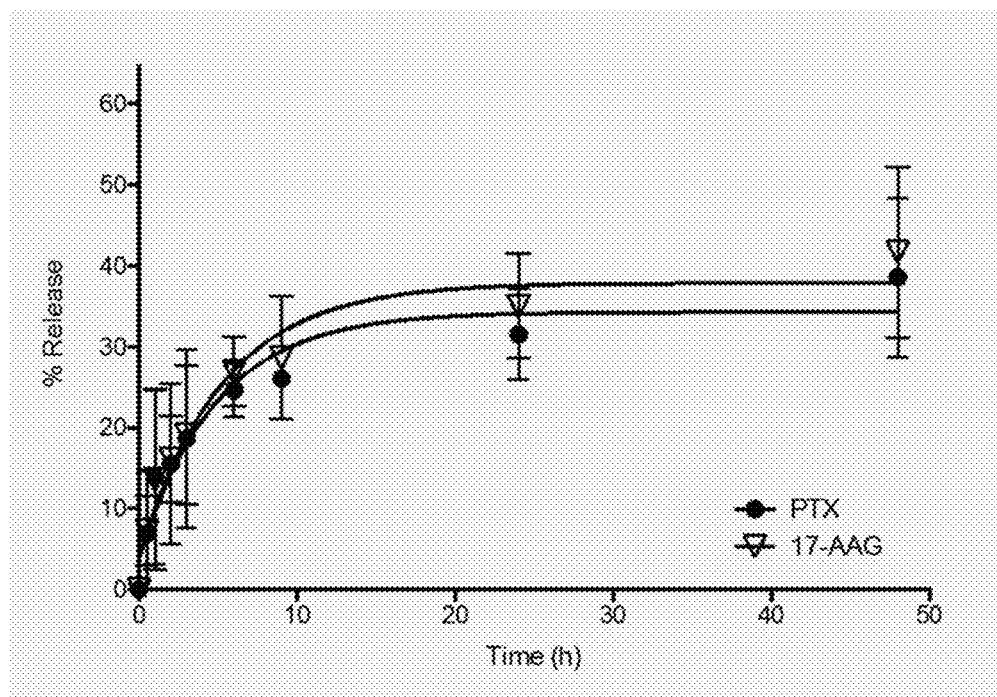
Figure 4C:
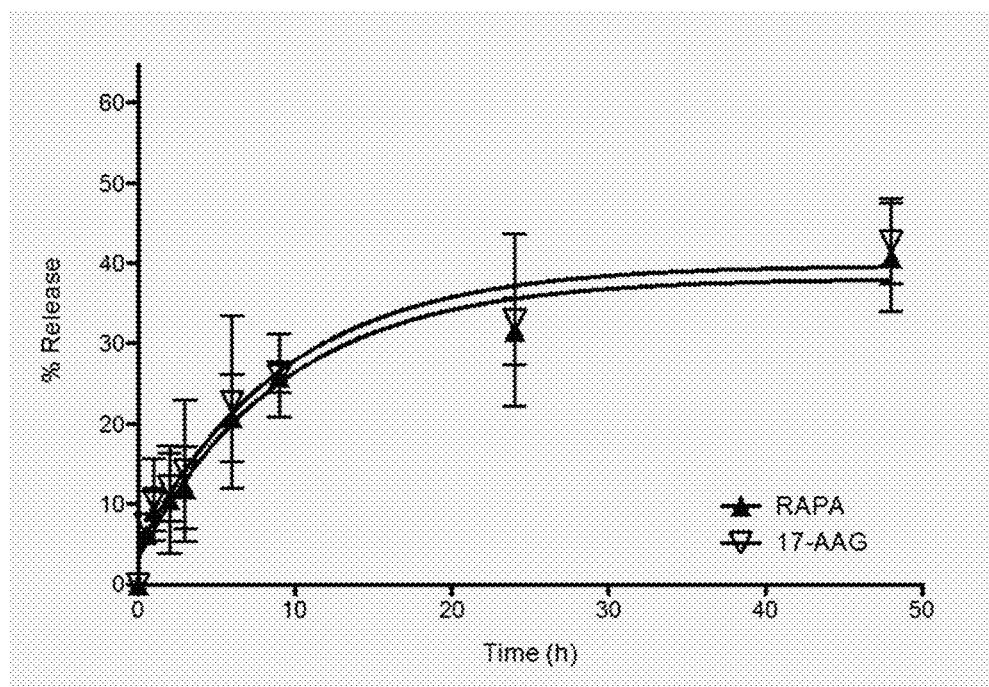

Two drug thermogels were then prepared according to the procedure described in Example 1. The following two drug thermogel were evaluated at 37° C.): PTX/RAPA (6 mg/3 mg in 90 mg polymer), PTX/17-AAG (6 mg/6 mg in 120 mg polymer), and RAPA/17-AAG (3 mg/6 mg in 90 mg polymer) in 1 mL water (see Table 2-3 and FIG. 4).

Thus, for the combinations of PTX/RAPA, PTX/17-AAG, and RAPA/17-AAG, the thermogel provided a controlled release of the actives at substantially the same rates, which can significantly aid clinical applications of the drugs because of the similar release rates.

This example demonstrates that a PLGA-PEG-PLGA thermogel provides a high loading capacity for two-drug combinations of PTX/RAPA, PTX/17-AAG, and RAPA/17-AAG; undergoes successful sol-gel transition at body temperature; and shows equivalent rates of drug release that can provide synergistic anticancer activity.

Example 3

Gel Degradation and Toxicity In Vivo

Intraperitoneal (IP) and intravenous (IV) injections of normal nude mice were performed using a Triogel formulation (prepared as disclosed above) and Triolimus micelle formulation (PEG-b-PLA micelles). Both the Triogel and Triolimus injections included drug concentrations of 6.0/6.0/3.0 mg/kg of PTX/17-AAG/RAPA at about 400 µL/animal. Both formulations exhibited purple coloring due to the presence of 17-AAG.

Figure 5:
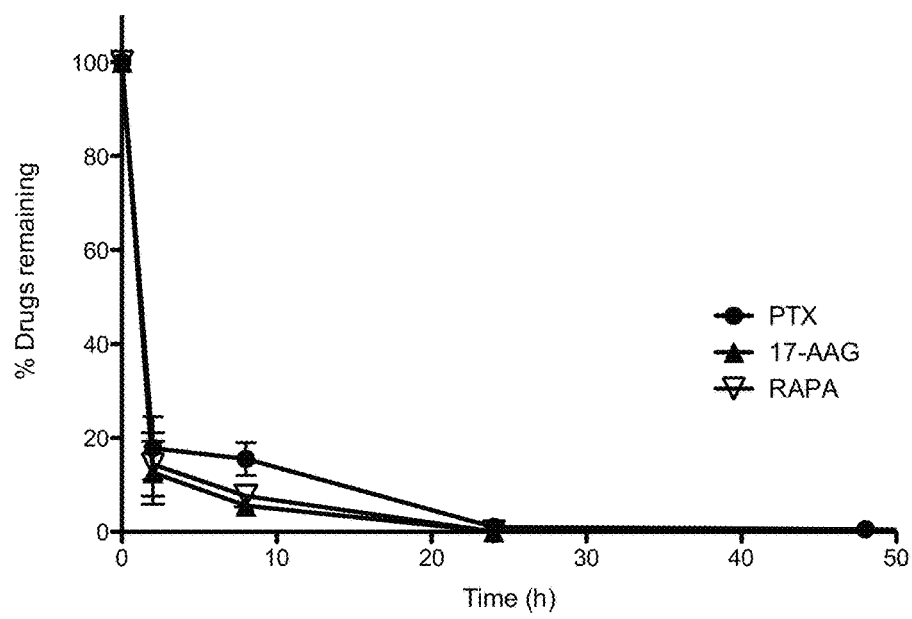
FIG. 5. Semi-quantitative drug contents remaining in Triogel in peritoneum of xenograft model.

Two hours post Triogel IP injection, gels were observed in the gaps and on the surface of organs. At two hours post Triolimus IP injection, no difference in peritoneal cavity appearance was found (no visual appearance of drug components residing in gaps or on the surface of the organs). At eight hours post Triogel IP injection, gels were observed near the organs located deeper from the abdominal surface. In the corresponding Triolimus animals, no visual appearance of the drugs in similar locations was found. At both 24 and 48 hours post Triogel IP injection, gels were observed near the organs located deeper from the abdominal surface. The gel visually decreased in amount over time and at 48 hours post Triogel IP injection, only one in three animals bore gel fragments in the peritoneum. The percent of drug contents observed over time in the Triogel IP injected animals is shown in FIG. 5.

Figure 6:
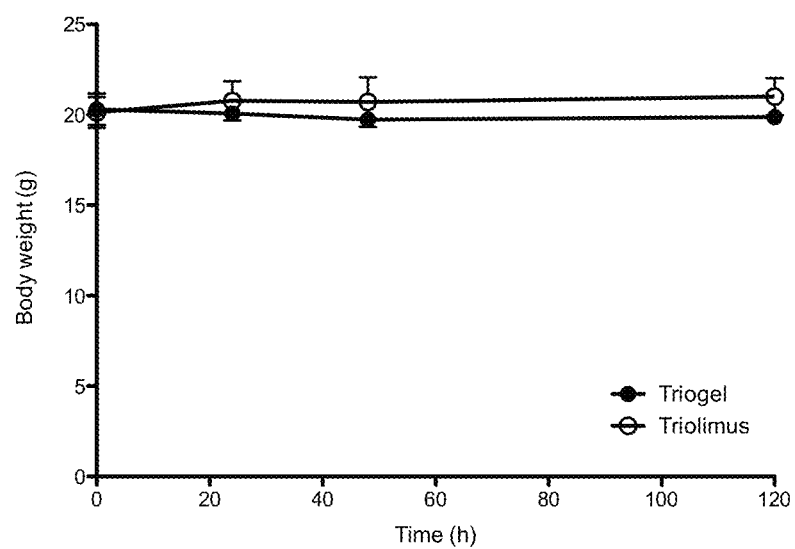
FIG. 6. Acute toxicity of Triogel and Triolimus.

As shown in FIG. 6, neither the Triogel formulation nor Triolimus formulation shows acute toxicity.

TABLE 2-3

| Release Kinetics Data of Two Drug Compositions. | | | | | |
|---|---|---|---|---|---|
| Drug (n = 3) | PTX+ | RAPA | PTX+ | 17-AAG | RAPA+ | 17-AAG |
| k | 0.1035 ± 0.0354 | 0.1163 ± 0.0490 | 0.2037 ± 0.0575 | 0.1906 ± 0.0443 | 0.1093 ± 0.0232 | 0.1093 ± 0.0265 |
| $R^2$ | 0.9258 | 0.8854 | 0.9365 | 0.9563 | 0.9692 | 0.9602 |
| Figure: | 5A | | 5B | | 5C | |

Example 4

Anticancer Efficacy In Vivo

Figure 7A:
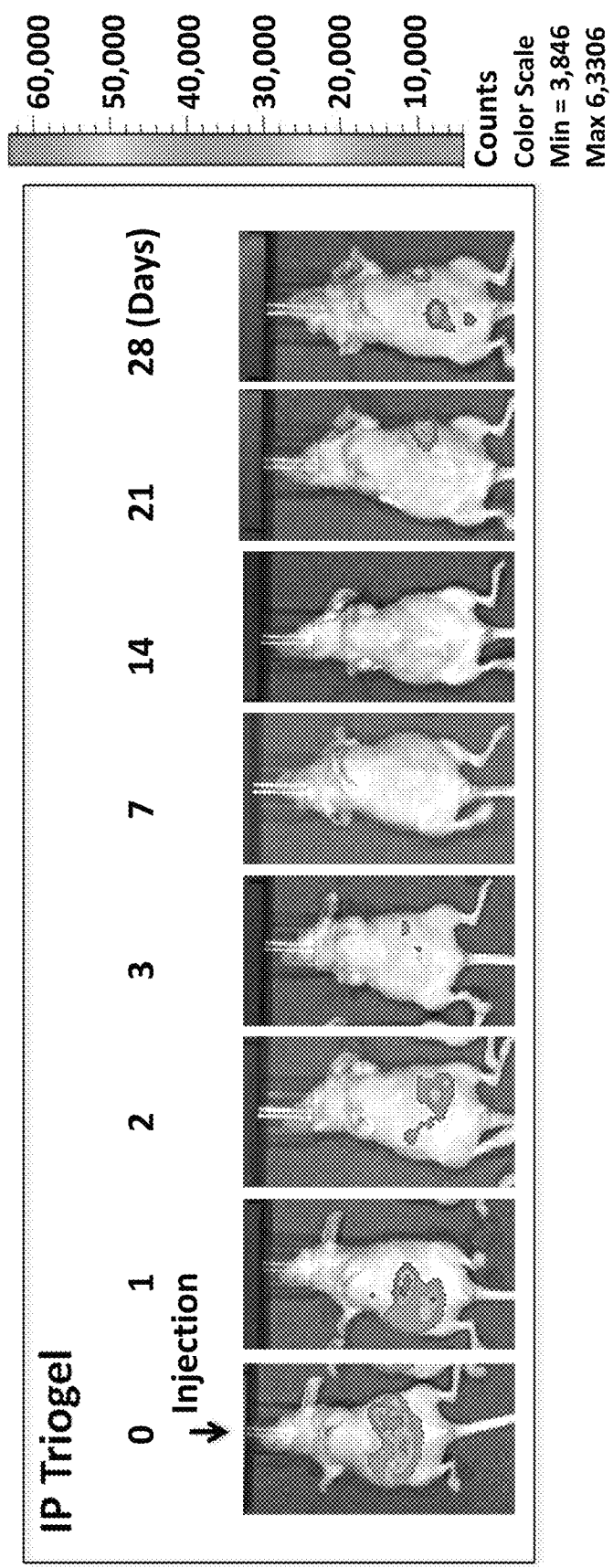
FIGS. 7A-E. Non-invasive bioluminescence imaging and treatment assessment for an ES-2-luc ovarian cancer model.
Figure 7B:
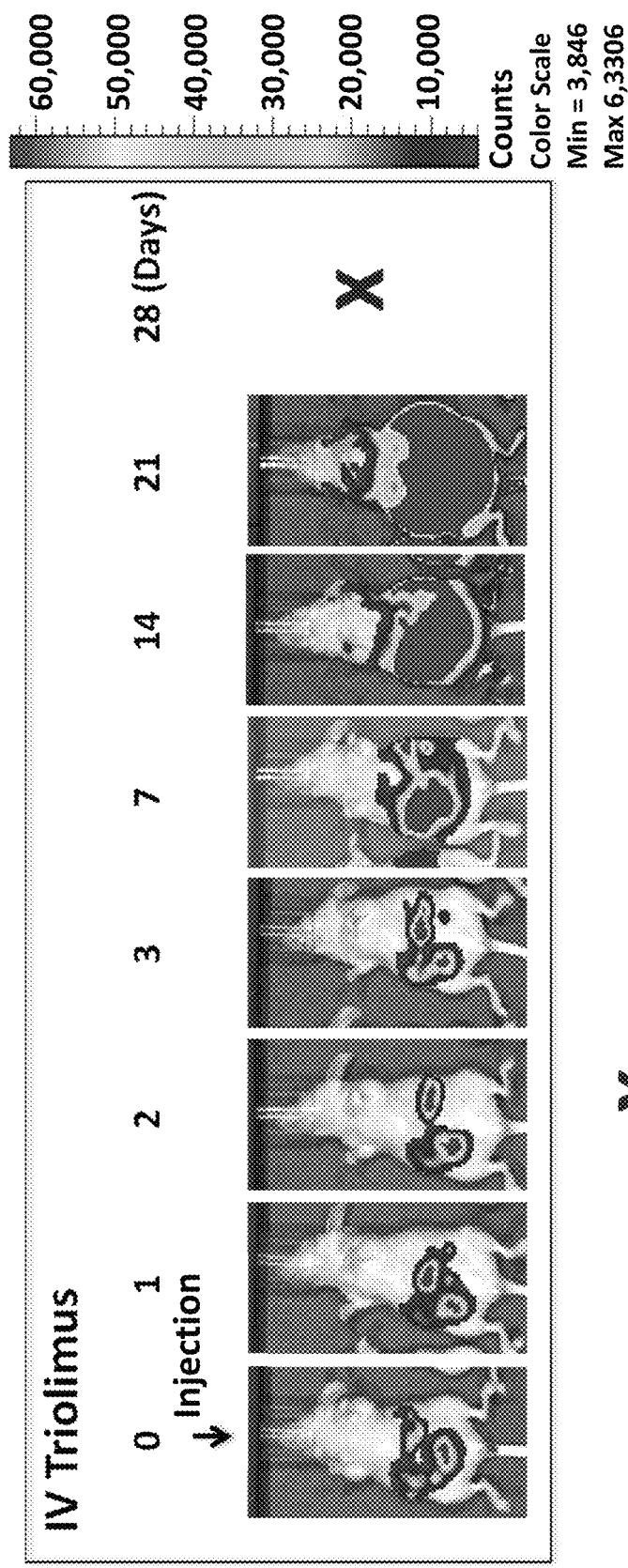
Figure 7C:
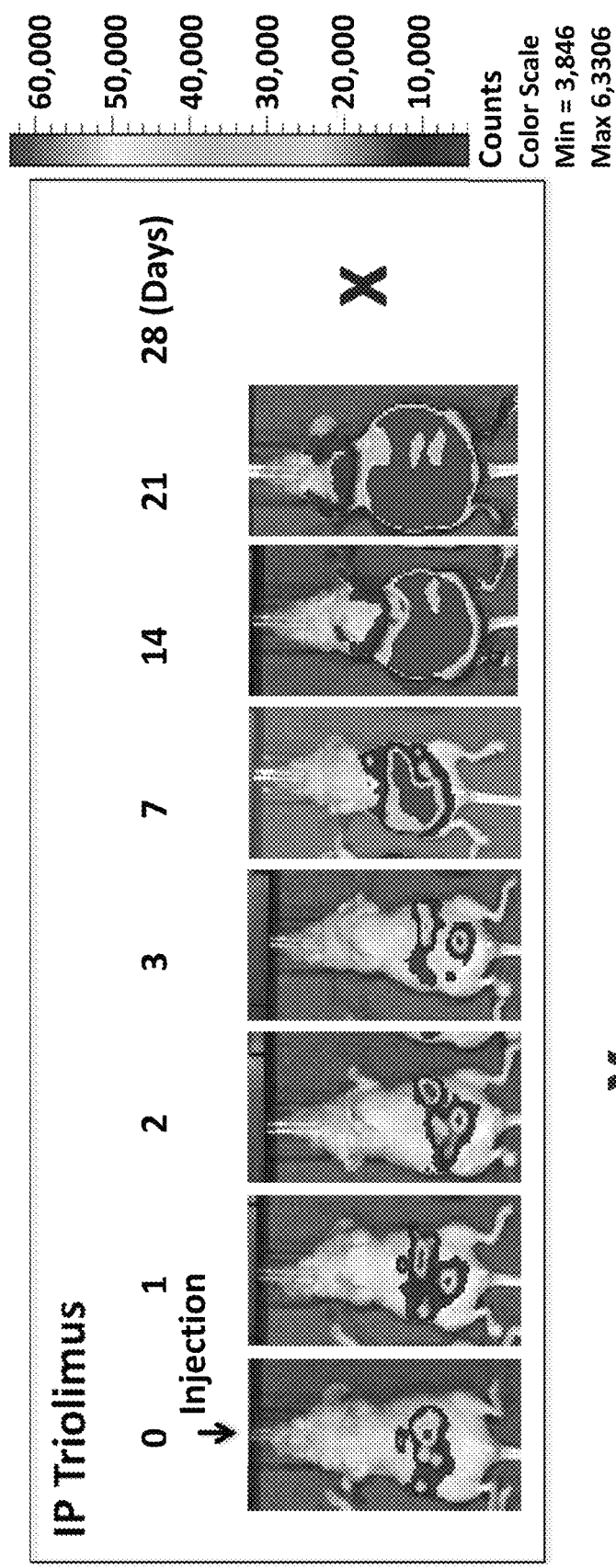
Figure 7D:
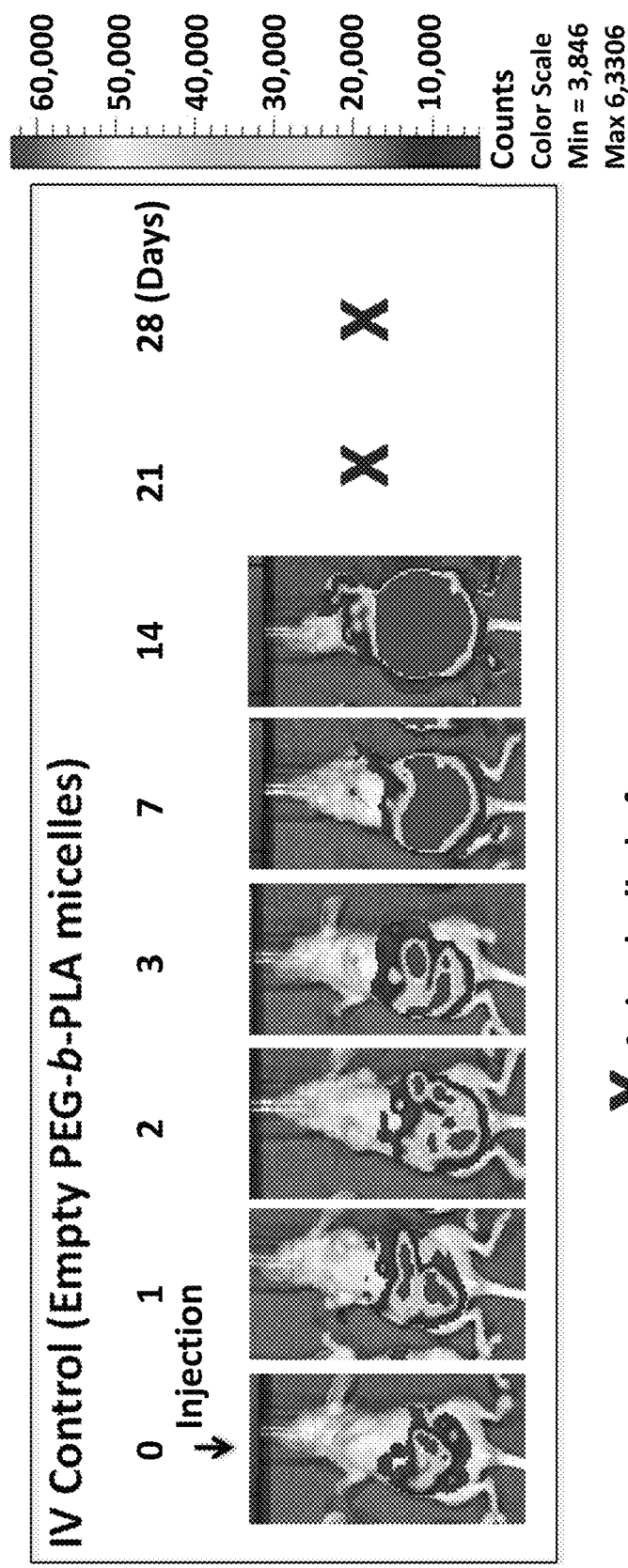
Figure 7E:
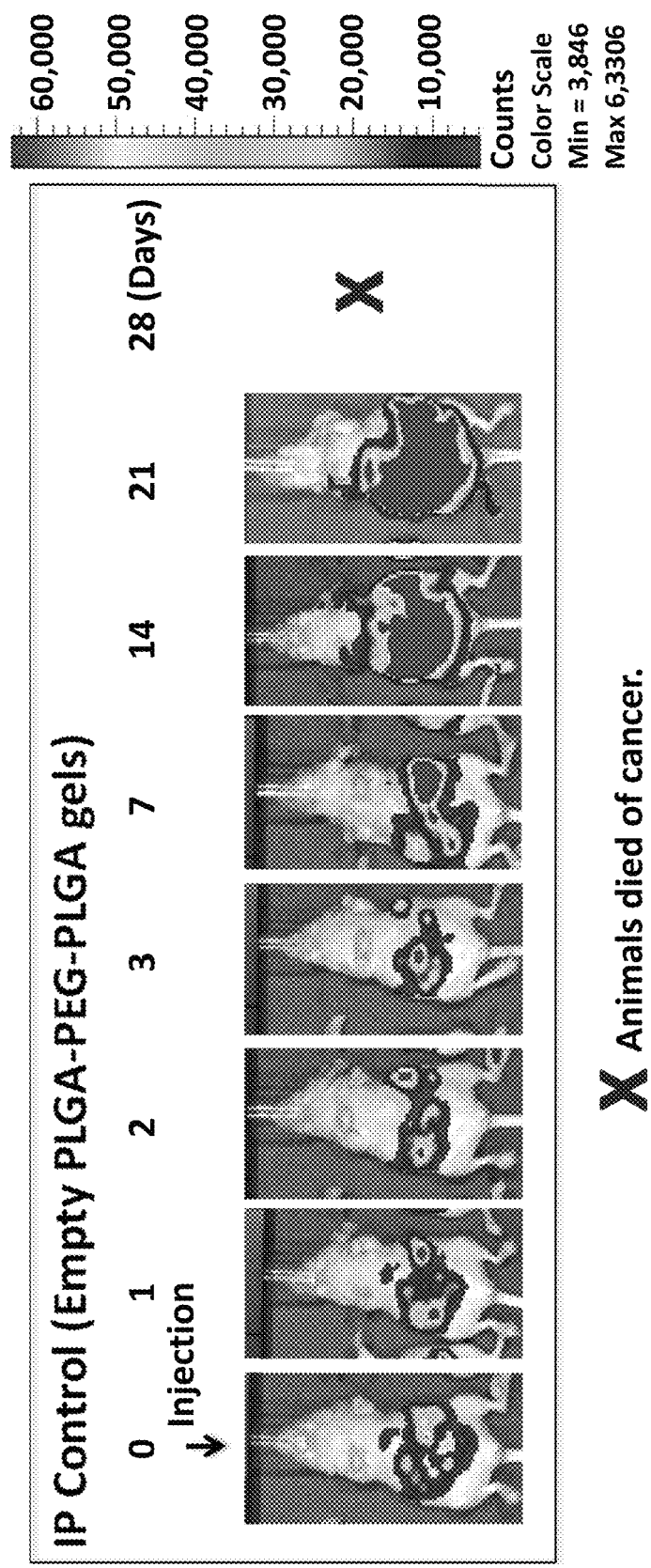

Intraperitoneal (IP) and intravenous (IV) injections of ES-2-luc human ovarian cancer-bearing nude mice were performed using a Triogel formulation (prepared as disclosed above) and Triolimus micelle formulation (PEG-b-PLA micelles). Both the Triogel (IP) and Triolimus (IP and IV) injections included drug concentrations of 60/60/30 mg/kg of PTX/17-AAG/RAPA at about 400 μL/animal for IP injections and about 200 μL/animal for IV injections. FIGS. 7A-E show non-invasive bioluminescence imaging and treatment assessment for an ES-2-luc ovarian cancer model. Bioluminescence signals represent ES-2-luc ovarian cancer cells, tissues, and ascites. FIG. 7A shows the results of an IP Triogel injection. FIG. 7B shows an IV Triolimus injection and FIG. 7C an IP Triolimus injection. FIGS. 7D and 7E are controls (IV injection of empty PEG-b-PLA micelles and IP injection of empty PLGA-PEG-PLGA gels, respectively).

Figure 8:
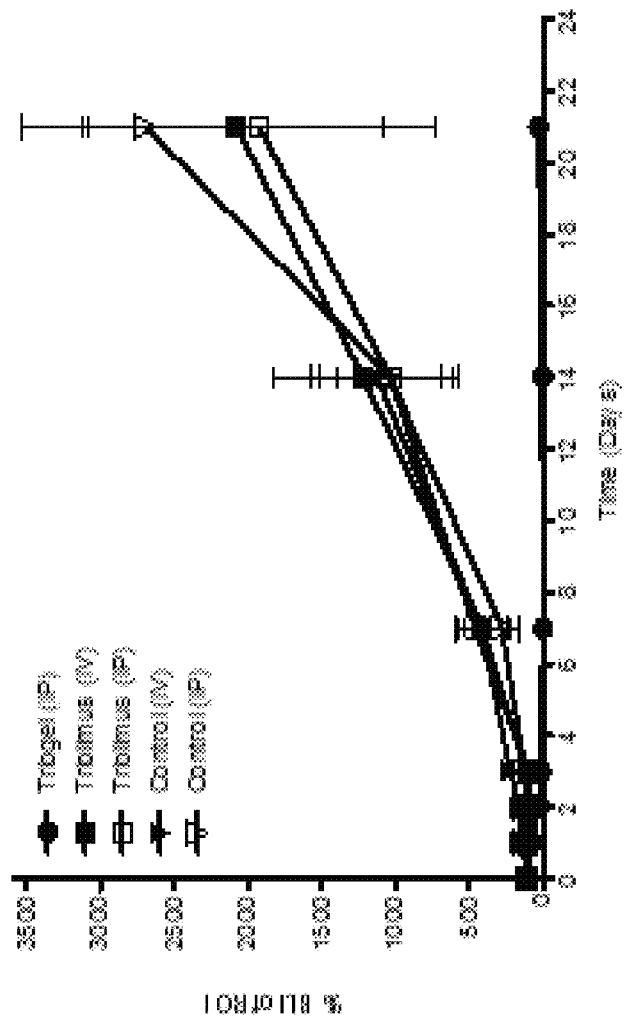
FIG. 8. Percent tumor burden calculated based on bioluminescence intensity in whole-body images.
Figure 9:
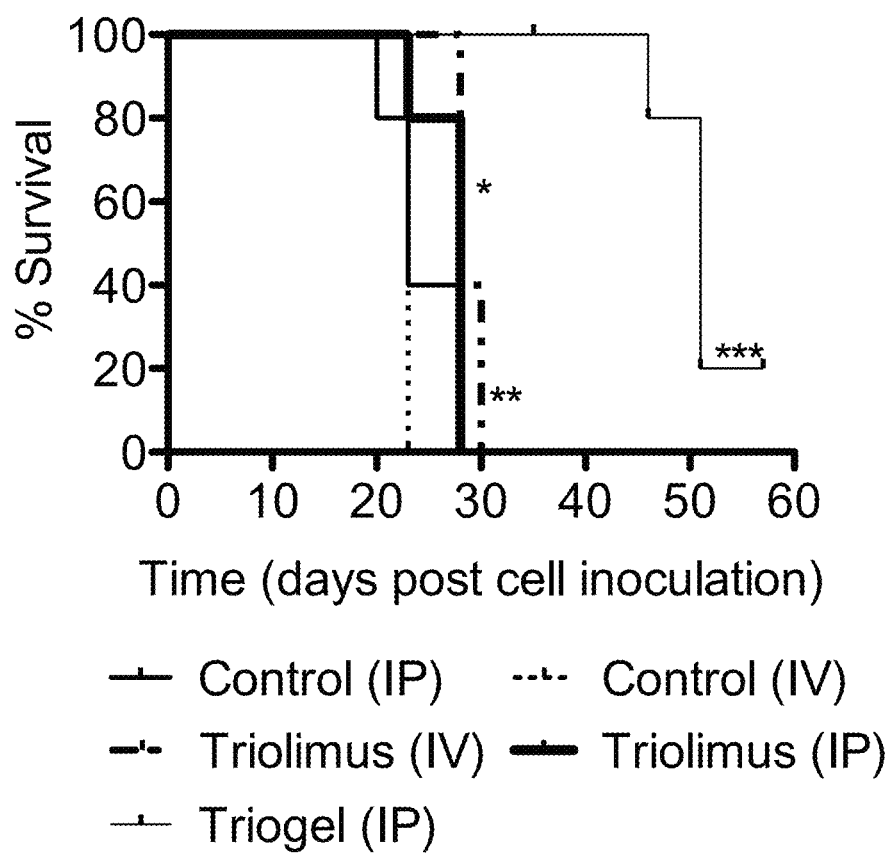
FIG. 9. Percent survival rate of an ES-2-luc ovarian cancer model upon treatments.

FIG. 8 displays percent tumor burden calculated based on bioluminescence intensity in whole-body images. A single IP injection of Triogel at 60/60/30 mg/kg of PTX/17-AAG/RAPA in human ovarian cancer-bearing IP metastatic animal model (ES-2-luc xenograft) decreased tumor burden to 32% (considering tumor burden at day 0 is 100%) whereas animals in control group increased tumor burden to 1100% at day 21 post injection of formulation. A single IV or IP injection of Triolimus at 60/60/30 mg/kg of PTX/17-AAG/RAPA did not show anticancer efficacy in ES-2-luc xenograft model. A single IP injection of Triogel at 60/60/30 mg/kg of PTX/17-AAG/RAPA in ES-2-luc xenograft model significantly prolonged animal survival. FIG. 9 shows percent survival rate of an ES-2-luc ovarian cancer model upon treatments.

PLGA-b-PEG-b-PLGA thermogels provides a high loading of PTX, 17-AAG, and RADA, undergoes successful sol-gel transition as temperature increases, and shows sustained release of contents at body temperature, leading to the heightened anticancer efficacy and prolonged survival of a peritoneal metastatic ovarian cancer model.

While specific embodiments have been described above with reference to the disclosed embodiments and examples, such embodiments are only illustrative and do not limit the scope of the invention. Changes and modifications can be made in accordance with ordinary skill in the art without departing from the invention in its broader aspects as defined in the following claims.

All publications, patents, and patent documents are incorporated by reference herein, as though individually incorporated by reference. No limitations inconsistent with this disclosure are to be understood therefrom. The invention has been described with reference to various specific and preferred embodiments and techniques. However, it should be understood that many variations and modifications may be made while remaining within the spirit and scope of the invention.

What is claimed is:

1. A composition comprising a PLGA-PEG-PLGA triblock copolymer, water, and a combination of therapeutic agents,
   wherein:
      the PLGA-PEG-PLGA triblock copolymer has an average molecular weight of about 3 kDa to about 5 kDa, a total PLGA content of about 50 wt % to about 85 wt % based on total weight of the PLGA-PEG-PLGA triblock copolymer, and a concentration range of about 3 wt % to about 30 wt %; and
      the combination of therapeutic agents comprises about 4 mg/mL to about 8 mg/mL of paclitaxel, about 4 mg/mL to about 8 mg/mL of 17-AAG, and about 2 mg/mL to about 6 mg/mL of rapamycin.

2. The composition of claim 1, wherein the PLGA-PEG-PLGA triblock copolymer is a $PLGA_{1.5K}$-$PEG_{1K}$-$PLGA_{1.5K}$ triblock copolymer.

3. The composition of claim 1, wherein the concentration of the combination of therapeutic agents in the composition is about 9 mg/mL to about 20 mg/mL.

4. The composition of claim 1, wherein the composition has a polydispersity index of about 0.3 to about 0.5.

5. The composition of claim 1, wherein the composition is a non-flowing thermosensitive hydrogel at and above 22° C. and a free-flowing solution below about 10° C.

6. The composition of claim 1, wherein the sum of the molecular weights of the PLGA blocks of the PLGA-PEG-PLGA triblock copolymer is more than twice the molecular weight of the PEG block and the PLGA-PEG-PLGA triblock copolymer has a concentration range of about 10 wt % to about 30 wt %.

7. The composition of claim 1, wherein the drug release $t_{1/2}$ of the composition at 37° C. is about 10 hours, and each of the drugs of the composition at 37° C. has equivalent drug release kinetics.

8. A method for killing or inhibiting the growth of cancer cells comprising contacting cancer cells with an effective lethal or inhibitory amount of a composition of claim 1, wherein the cancer cells are brain cancer cells, breast cancer cells, esophageal cancer cells, head and neck cancer cells, ovarian cancer cells, or pancreatic cancer cells.

9. The method of claim 8, wherein the composition is in the form of a non-flowing gel and each of the drugs of the non-flowing gel has equivalent drug release kinetics.

10. A method of treating a solid tumor comprising locally administering an effective anticancer amount of a composition of claim 1 to a subject in need thereof, wherein the amount of therapeutic agents administered to the subject would cause systemic toxicity if administered orally or intravenously, and wherein the local administration does not cause systemic toxicity.

11. A method of preparing a composition comprising:
   combining an aqueous solution of PLGA-PEG-PLGA triblock copolymer and an alcoholic solution of a combination of therapeutic agents;
   lyophilizing the mixture to provide a powder or cake; and
   rehydrating the powder or cake with water at a temperature of less than about 10° C., to provide the composition;
   wherein:
      the PLGA-PEG-PLGA triblock copolymer has an average molecular weight of about 3 kDa to about 5 kDa, a total PLGA content of about 50 wt % to about 85 wt % based on total weight of the PLGA-PEG-PLGA triblock copolymer, and a concentration range of about 3 wt % to about 30 wt %; and
      the combination of therapeutic agents comprises about 4 mg/mL to about 8 mg/mL of paclitaxel, about 4 mg/mL to about 8mg/mL of 17-AAG, and about 2 mg/mL to about 6 mg/mL of rapamycin.

12. The method of claim 11, wherein the PLGA-PEG-PLGA triblock copolymer is a $PLGA_{1.5K}$-$PEG_{1K}$-$PLGA_{1.5K}$ triblock copolymer and the alcohol of the alcoholic solution is t-butanol.

13. The method of claim 11, wherein the sum of the molecular weights of the PLGA blocks of the PLGA-PEG-PLGA triblock copolymer is more than twice the molecular weight of the PEG block and the PLGA-PEG-PLGA triblock copolymer has a concentration range of about 10 wt % to about 30 wt %.

14. A composition comprising a PLGA-PEG-PLGA triblock copolymer, water, and a combination of therapeutic agents,
wherein:
the PLGA-PEG-PLGA triblock copolymer has an average molecular weight of about 3 kDa to about 5 kDa, a total PLGA content of about 50 wt % to about 85 wt % based on total weight of the PLGA-PEG-PLGA triblock copolymer, and a concentration range of about 3 wt % to about 30 wt %; and
the combination of therapeutic agents comprises:
about 4 mg/mL to about 8 mg/mL of paclitaxel and about 2 mg/mL to about 6 mg/mL of rapamycin;
about 4 mg/mL to about 8 mg/mL of paclitaxel and about 4 mg/mL to about 8 mg/mL of 17-AAG;
about 4 mg/mL to about 8 mg/mL of 17-AAG and about 2 mg/mL to about 6 mg/mL of rapamycin; or
about 4 mg/mL to about 8 mg/mL of cyclopamine and about 4 mg/mL to about 8 mg/mL of 17-AAG.

15. The composition of claim 14, wherein the combination of therapeutic agents comprises about 4 mg/mL to about 8 mg/mL of paclitaxel and about 2 mg/mL to about 6 mg/mL of rapamycin.

16. The composition of claim 14, wherein the combination of therapeutic agents comprises about 4 mg/mL to about 8 mg/mL of paclitaxel and about 4 mg/mL to about 8 mg/mL of 17-AAG.

17. The composition of claim 14, wherein the combination of therapeutic agents comprises about 4 mg/mL to about 8 mg/mL of 17-AAG and about 2 mg/mL to about 6 mg/mL of rapamycin.

18. The composition of claim 14, wherein the PLGA-PEG-PLGA triblock copolymer is a $PLGA_{1.5K}$-$PEG_{1K}$-$PLGA_{1.5K}$ triblock copolymer.

19. The composition of claim 14, wherein the composition has a polydispersity index of about 0.3 to about 0.5.

20. The composition of claim 14, wherein the composition is a non-flowing thermosensitive hydrogel at and above 22° C. and a free-flowing solution below about 10° C.

21. The composition of claim 14, wherein the sum of the molecular weights of the PLGA blocks of the PLGA-PEG-PLGA triblock copolymer is more than twice the molecular weight of the PEG block and the PLGA-PEG-PLGA triblock copolymer has a concentration range of about 10 wt % to about 30 wt %.

22. The composition of claim 14, wherein the drug release tv2 of the composition at 37° C. is about 10 hours, and each of the drugs of the composition at 37° C. has equivalent drug release kinetics.

23. A method for killing or inhibiting the growth of cancer cells comprising contacting cancer cells with an effective lethal or inhibitory amount of a composition of claim 14, wherein the cancer cells are brain cancer cells, breast cancer cells, esophageal cancer cells, head and neck cancer cells, ovarian cancer cells, or pancreatic cancer cells.

24. The method of claim 23, wherein the composition is in the form of a non-flowing gel and each of the drugs of the non-flowing gel has equivalent drug release kinetics.

25. A method of treating a solid tumor comprising locally administering an effective anticancer amount of a composition of claim 14 to a subject in need thereof, wherein the amount of therapeutic agents administered to the subject would cause systemic toxicity if administered orally or intravenously, and wherein the local administration does not cause systemic toxicity.

* * * * *